United States Patent
Botvinnik et al.

(10) Patent No.: US 7,833,322 B2
(45) Date of Patent: Nov. 16, 2010

(54) AIR TREATMENT APPARATUS HAVING A VOLTAGE CONTROL DEVICE RESPONSIVE TO CURRENT SENSING

(75) Inventors: Igor Y. Botvinnik, Novato, CA (US); Charles E. Taylor, Punta Gorda, FL (US)

(73) Assignee: Sharper Image Acquisition LLC, New York, NY (US)

(*) Notice: Subject to any disclaimer, the term of this patent is extended or adjusted under 35 U.S.C. 154(b) by 556 days.

(21) Appl. No.: 11/679,606

(22) Filed: Feb. 27, 2007

(65) Prior Publication Data

US 2007/0210734 A1 Sep. 13, 2007

Related U.S. Application Data

(60) Provisional application No. 60/777,943, filed on Feb. 28, 2006.

(51) Int. Cl.
 *B03C 3/68* (2006.01)
(52) U.S. Cl. ............... 96/21; 95/6; 95/7; 96/22; 96/23; 96/24; 96/25; 96/26; 323/903
(58) Field of Classification Search ............... 96/21–24, 96/80–82, 25, 26; 95/6, 7; 323/304, 318, 323/903; 361/225–235
See application file for complete search history.

(56) References Cited

U.S. PATENT DOCUMENTS

| | | | |
|---|---|---|---|
| 653,421 A | 7/1900 | Lorey | |
| 895,729 A | 8/1908 | Carlborg | |
| 995,958 A | 6/1911 | Goldberg | |
| 1,791,338 A | 2/1931 | Wintermute | |
| 1,869,335 A | 7/1932 | Day | |
| 1,882,949 A | 10/1932 | Ruder | |
| 2,129,783 A | 9/1938 | Penney | |
| 2,247,409 A | 7/1941 | Roper | |
| 2,327,588 A | 8/1943 | Bennett | |
| 2,359,057 A | 9/1944 | Skinner | |
| 2,509,548 A | 5/1950 | White | |
| 2,590,447 A | 3/1952 | Nord et al. | |
| 2,907,403 A * | 10/1959 | Foley | 96/23 |
| 2,949,550 A | 8/1960 | Brown | |
| 2,978,066 A | 4/1961 | Nodolf | |
| 3,018,394 A | 1/1962 | Brown | |
| 3,026,964 A | 3/1962 | Penney | |
| 3,374,941 A | 3/1968 | Okress | |
| 3,412,530 A | 11/1968 | Cardiff | |
| 3,518,462 A | 6/1970 | Brown | |
| 3,540,191 A | 11/1970 | Herman | |
| 3,581,470 A | 6/1971 | Aitkenhead et al. | |
| 3,602,805 A * | 8/1971 | Vukasovic | 323/242 |

(Continued)

FOREIGN PATENT DOCUMENTS

CN 2111112 U 7/1972

(Continued)

*Primary Examiner*—Richard L Chiesa

(57) ABSTRACT

An air treatment apparatus that includes an electrode assembly, a voltage supply, a current sensing device operably coupled to the electrode assembly, and a voltage control device coupled to the current sensing device and the voltage supply. The voltage control device is configured to regulate the level of voltage based on the level of current flowing through the current sensing device to maintain the voltage and current in the electrode assembly within designated ranges.

14 Claims, 10 Drawing Sheets

U.S. PATENT DOCUMENTS

| | | | |
|---|---|---|---|
| 3,622,839 A * | 11/1971 | Abrams et al. ............. 96/21 |
| 3,638,058 A | 1/1972 | Fritzius |
| 3,744,216 A | 7/1973 | Halloran |
| 3,745,749 A * | 7/1973 | Gelfand ..................... 96/21 |
| 3,806,763 A | 4/1974 | Masuda |
| 3,877,896 A * | 4/1975 | Muskovac ................. 96/22 |
| 3,892,927 A | 7/1975 | Lindenberg |
| 3,945,813 A | 3/1976 | Iinoya et al. |
| 3,958,960 A | 5/1976 | Bakke |
| 3,958,961 A | 5/1976 | Bakke |
| 3,958,962 A | 5/1976 | Hayashi |
| 3,981,695 A | 9/1976 | Fuchs |
| 3,984,215 A | 10/1976 | Zucker |
| 3,988,131 A | 10/1976 | Kanazawa et al. |
| 4,007,024 A | 2/1977 | Sallee et al. |
| 4,052,177 A | 10/1977 | Kide |
| 4,056,372 A | 11/1977 | Hayashi |
| 4,070,163 A | 1/1978 | Kolb et al. |
| 4,074,983 A | 2/1978 | Bakke |
| 4,092,134 A | 5/1978 | Kikuchi |
| 4,097,252 A | 6/1978 | Kirchhoff et al. |
| 4,102,654 A | 7/1978 | Pellin |
| 4,104,042 A | 8/1978 | Brozenick |
| 4,110,086 A | 8/1978 | Schwab et al. |
| 4,119,415 A | 10/1978 | Hayashi et al. |
| 4,126,434 A | 11/1978 | Keiichi |
| 4,138,233 A | 2/1979 | Masuda |
| 4,147,522 A | 4/1979 | Gonas et al. |
| 4,155,792 A | 5/1979 | Gelhaar et al. |
| 4,171,975 A | 10/1979 | Kato et al. |
| 4,185,971 A | 1/1980 | Isahaya |
| 4,189,308 A | 2/1980 | Feldman |
| 4,205,969 A | 6/1980 | Matsumoto |
| 4,209,306 A | 6/1980 | Feldman et al. |
| 4,218,225 A | 8/1980 | Kirchhoff et al. |
| 4,225,323 A | 9/1980 | Zarchy et al. |
| 4,227,894 A | 10/1980 | Proynoff |
| 4,231,766 A | 11/1980 | Spurgin |
| 4,232,355 A | 11/1980 | Finger et al. |
| 4,244,710 A | 1/1981 | Burger |
| 4,244,712 A | 1/1981 | Tongret |
| 4,251,234 A | 2/1981 | Chang |
| 4,253,852 A | 3/1981 | Adams |
| 4,259,093 A | 3/1981 | Vlastos et al. |
| 4,259,452 A | 3/1981 | Yukuta et al. |
| 4,259,707 A | 3/1981 | Penney |
| 4,264,343 A | 4/1981 | Natarajan et al. |
| 4,266,948 A | 5/1981 | Teague et al. |
| 4,282,014 A | 8/1981 | Winkler et al. |
| 4,284,420 A | 8/1981 | Borysiak |
| 4,289,504 A | 9/1981 | Scholes |
| 4,293,319 A | 10/1981 | Claassen, Jr. |
| 4,308,036 A | 12/1981 | Zahedi et al. |
| 4,315,188 A | 2/1982 | Cerny et al. |
| 4,318,718 A | 3/1982 | Utsumi et al. |
| 4,338,560 A | 7/1982 | Lemley |
| 4,342,571 A | 8/1982 | Hayashi |
| 4,349,359 A | 9/1982 | Fitch et al. |
| 4,351,648 A | 9/1982 | Penney |
| 4,354,861 A | 10/1982 | Kalt |
| 4,357,150 A | 11/1982 | Masuda et al. |
| 4,362,632 A | 12/1982 | Jacob |
| 4,363,072 A | 12/1982 | Coggins |
| 4,366,525 A | 12/1982 | Baumgartner |
| 4,369,776 A | 1/1983 | Roberts |
| 4,375,364 A | 3/1983 | Van Hoesen et al. |
| 4,380,900 A | 4/1983 | Linder et al. |
| 4,386,395 A | 5/1983 | Francis, Jr. |
| 4,391,614 A | 7/1983 | Rozmus |
| 4,394,239 A | 7/1983 | Kitzelmann et al. |
| 4,405,342 A | 9/1983 | Bergman |
| 4,406,671 A | 9/1983 | Rozmus |
| 4,412,850 A | 11/1983 | Kurata et al. |
| 4,413,225 A | 11/1983 | Donig et al. |
| 4,414,603 A | 11/1983 | Masuda |
| 4,435,190 A | 3/1984 | Taillet et al. |
| 4,440,552 A | 4/1984 | Uchiya et al. |
| 4,443,234 A | 4/1984 | Carlsson |
| 4,445,911 A | 5/1984 | Lind |
| 4,477,263 A | 10/1984 | Shaver et al. |
| 4,477,268 A | 10/1984 | Kalt |
| 4,481,017 A | 11/1984 | Furlong |
| 4,496,375 A | 1/1985 | Levantine |
| 4,502,002 A | 2/1985 | Ando |
| 4,505,724 A | 3/1985 | Baab |
| 4,509,958 A | 4/1985 | Masuda et al. |
| 4,514,780 A | 4/1985 | Brussee et al. |
| 4,515,982 A | 5/1985 | Lechtken et al. |
| 4,516,991 A | 5/1985 | Kawashima |
| 4,521,229 A | 6/1985 | Baker et al. |
| 4,522,634 A | 6/1985 | Frank |
| 4,534,776 A | 8/1985 | Mammel et al. |
| 4,536,698 A | 8/1985 | Shevalenko et al. |
| 4,544,382 A | 10/1985 | Taillet et al. |
| 4,555,252 A | 11/1985 | Eckstein |
| 4,569,684 A | 2/1986 | Ibbott |
| 4,582,961 A | 4/1986 | Frederiksen |
| 4,587,475 A | 5/1986 | Finney, Jr. et al. |
| 4,588,423 A | 5/1986 | Gillingham et al. |
| 4,590,042 A | 5/1986 | Drage |
| 4,597,780 A | 7/1986 | Reif |
| 4,597,781 A | 7/1986 | Spector |
| 4,600,411 A | 7/1986 | Santamaria |
| 4,601,733 A | 7/1986 | Ordines et al. |
| 4,604,174 A | 8/1986 | Bollinger et al. |
| 4,614,573 A | 9/1986 | Masuda |
| 4,623,365 A | 11/1986 | Bergman |
| 4,626,261 A | 12/1986 | Jorgensen |
| 4,632,135 A | 12/1986 | Lenting et al. |
| 4,632,746 A | 12/1986 | Bergman |
| 4,636,981 A | 1/1987 | Ogura |
| 4,643,744 A | 2/1987 | Brooks |
| 4,643,745 A | 2/1987 | Sakakibara et al. |
| 4,647,836 A | 3/1987 | Olsen |
| 4,650,648 A | 3/1987 | Beer et al. |
| 4,656,010 A | 4/1987 | Leitzke et al. |
| 4,657,738 A | 4/1987 | Kanter et al. |
| 4,659,342 A | 4/1987 | Lind |
| 4,662,903 A | 5/1987 | Yanagawa |
| 4,666,474 A | 5/1987 | Cook |
| 4,668,479 A | 5/1987 | Manabe et al. |
| 4,670,026 A | 6/1987 | Hoenig |
| 4,673,416 A | 6/1987 | Sakakibara et al. |
| 4,674,003 A | 6/1987 | Zylka |
| 4,680,496 A | 7/1987 | Letournel et al. |
| 4,686,370 A | 8/1987 | Blach |
| 4,689,056 A | 8/1987 | Noguchi et al. |
| 4,691,829 A | 9/1987 | Auer |
| 4,692,174 A | 9/1987 | Gelfand et al. |
| 4,693,869 A | 9/1987 | Pfaff |
| 4,694,376 A | 9/1987 | Gesslauer |
| 4,702,752 A | 10/1987 | Yanagawa |
| 4,713,092 A | 12/1987 | Kikuchi et al. |
| 4,713,093 A | 12/1987 | Hansson |
| 4,713,724 A | 12/1987 | Voelkel |
| 4,715,870 A | 12/1987 | Masuda et al. |
| 4,725,289 A | 2/1988 | Quintilian |
| 4,726,812 A | 2/1988 | Hirth |
| 4,726,814 A | 2/1988 | Weitman |
| 4,736,127 A | 4/1988 | Jacobsen |
| 4,743,275 A | 5/1988 | Flanagan |
| 4,749,390 A | 6/1988 | Burnett et al. |
| 4,750,921 A | 6/1988 | Sugita et al. |
| 4,760,302 A | 7/1988 | Jacobsen |

| | | | | | | |
|---|---|---|---|---|---|---|
| 4,760,303 A | 7/1988 | Miyake | | 5,234,555 A | 8/1993 | Ibbott |
| 4,765,802 A | 8/1988 | Gombos et al. | | 5,248,324 A | 9/1993 | Hara |
| 4,771,361 A | 9/1988 | Varga | | 5,250,267 A | 10/1993 | Johnson et al. |
| 4,772,297 A | 9/1988 | Anzai | | 5,254,155 A | 10/1993 | Mensi |
| 4,779,182 A | 10/1988 | Mickal et al. | | 5,266,004 A | 11/1993 | Tsumurai et al. |
| 4,781,736 A | 11/1988 | Cheney et al. | | 5,271,763 A | 12/1993 | Jang |
| 4,786,844 A | 11/1988 | Farrell et al. | | 5,282,891 A | 2/1994 | Durham |
| 4,789,801 A | 12/1988 | Lee | | 5,290,343 A | 3/1994 | Morita et al. |
| 4,808,200 A | 2/1989 | Dallhammer et al. | | 5,296,019 A | 3/1994 | Oakley et al. |
| 4,811,159 A | 3/1989 | Foster, Jr. | | 5,302,190 A | 4/1994 | Williams |
| 4,822,381 A | 4/1989 | Mosley et al. | | 5,308,586 A | 5/1994 | Fritsche et al. |
| 4,853,005 A | 8/1989 | Jaisinghani et al. | | 5,311,420 A * | 5/1994 | Zarfoss et al. ................ 700/28 |
| 4,860,149 A * | 8/1989 | Johnston ..................... 361/79 | | 5,315,838 A | 5/1994 | Thompson |
| 4,869,736 A | 9/1989 | Ivester et al. | | 5,316,741 A | 5/1994 | Sewell et al. |
| 4,892,713 A | 1/1990 | Newman | | 5,330,559 A | 7/1994 | Cheney et al. |
| 4,929,139 A | 5/1990 | Vorreiter et al. | | 5,348,571 A | 9/1994 | Weber |
| 4,936,876 A * | 6/1990 | Reyes ............................. 95/6 | | 5,376,168 A | 12/1994 | Inculet |
| 4,940,470 A | 7/1990 | Jaisinghani et al. | | 5,378,978 A | 1/1995 | Gallo et al. |
| 4,940,894 A | 7/1990 | Morters | | 5,386,839 A | 2/1995 | Chen |
| 4,941,068 A | 7/1990 | Hofmann | | 5,395,430 A | 3/1995 | Lundgren et al. |
| 4,941,224 A | 7/1990 | Saeki et al. | | 5,401,301 A | 3/1995 | Schulmerich et al. |
| 4,944,778 A | 7/1990 | Yanagawa | | 5,401,302 A | 3/1995 | Schulmerich et al. |
| 4,954,320 A | 9/1990 | Birmingham et al. | | 5,403,383 A | 4/1995 | Jaisinghani |
| 4,955,991 A | 9/1990 | Torok et al. | | 5,405,434 A | 4/1995 | Inculet |
| 4,966,666 A | 10/1990 | Waltonen | | 5,407,469 A | 4/1995 | Sun |
| 4,967,119 A | 10/1990 | Torok et al. | | 5,407,639 A | 4/1995 | Watanabe et al. |
| 4,976,752 A | 12/1990 | Torok et al. | | 5,417,936 A | 5/1995 | Suzuki et al. |
| 4,978,372 A | 12/1990 | Pick | | 5,419,953 A | 5/1995 | Chapman |
| D315,598 S | 3/1991 | Yamamoto et al. | | 5,433,772 A | 7/1995 | Sikora |
| 5,003,774 A | 4/1991 | Leonard | | 5,435,817 A | 7/1995 | Davis et al. |
| 5,006,761 A | 4/1991 | Torok et al. | | 5,435,978 A | 7/1995 | Yokomi |
| 5,010,869 A | 4/1991 | Lee | | 5,437,713 A | 8/1995 | Chang |
| 5,012,093 A | 4/1991 | Shimizu | | 5,437,843 A | 8/1995 | Kuan |
| 5,012,094 A | 4/1991 | Hamade | | 5,445,798 A | 8/1995 | Ikeda et al. |
| 5,012,159 A | 4/1991 | Torok et al. | | 5,456,741 A * | 10/1995 | Takahara et al. ................ 96/22 |
| 5,022,979 A | 6/1991 | Hijikata et al. | | 5,466,279 A | 11/1995 | Hattori et al. |
| 5,024,685 A | 6/1991 | Torok et al. | | 5,468,454 A | 11/1995 | Kim |
| 5,030,254 A | 7/1991 | Heyen et al. | | 5,474,599 A | 12/1995 | Cheney et al. |
| 5,034,033 A | 7/1991 | Alsup et al. | | 5,484,472 A | 1/1996 | Weinberg |
| 5,037,456 A | 8/1991 | Yu | | 5,484,473 A | 1/1996 | Bontempi |
| 5,045,095 A | 9/1991 | You | | 5,492,678 A | 2/1996 | Ota et al. |
| 5,053,912 A | 10/1991 | Loreth et al. | | 5,501,844 A | 3/1996 | Kasting, Jr. et al. |
| 5,059,219 A | 10/1991 | Plaks et al. | | 5,503,808 A | 4/1996 | Garbutt et al. |
| 5,061,462 A | 10/1991 | Suzuki | | 5,503,809 A | 4/1996 | Coate et al. |
| 5,066,313 A | 11/1991 | Mallory, Sr. | | 5,505,914 A | 4/1996 | Tona-Serra |
| 5,068,811 A * | 11/1991 | Johnston et al. ............. 700/297 | | 5,508,008 A | 4/1996 | Wasser |
| 5,072,746 A | 12/1991 | Kantor | | 5,514,345 A | 5/1996 | Garbutt et al. |
| 5,076,820 A | 12/1991 | Gurvitz | | 5,516,493 A | 5/1996 | Bell et al. |
| 5,077,468 A | 12/1991 | Hamade | | 5,518,531 A | 5/1996 | Joannu |
| 5,077,500 A | 12/1991 | Torok et al. | | 5,520,887 A | 5/1996 | Shimizu et al. |
| 5,100,440 A | 3/1992 | Stahel et al. | | 5,525,310 A | 6/1996 | Decker et al. |
| RE33,927 E | 5/1992 | Fuzimura | | 5,529,613 A | 6/1996 | Yavnieli |
| D326,514 S | 5/1992 | Alsup et al. | | 5,529,760 A | 6/1996 | Burris |
| 5,118,942 A | 6/1992 | Hamade | | 5,532,798 A | 7/1996 | Nakagami et al. |
| 5,125,936 A | 6/1992 | Johansson | | 5,535,089 A | 7/1996 | Ford et al. |
| 5,136,461 A | 8/1992 | Zellweger | | 5,536,477 A | 7/1996 | Cha et al. |
| 5,137,546 A | 8/1992 | Steinbacher et al. | | 5,538,695 A | 7/1996 | Shinjo et al. |
| 5,141,529 A | 8/1992 | Oakley et al. | | 5,540,761 A | 7/1996 | Yamamoto |
| 5,141,715 A | 8/1992 | Sackinger et al. | | 5,542,967 A | 8/1996 | Ponizovsky et al. |
| D329,284 S | 9/1992 | Patton | | 5,545,379 A | 8/1996 | Gray |
| 5,147,429 A | 9/1992 | Bartholomew et al. | | 5,545,380 A | 8/1996 | Gray |
| 5,154,733 A | 10/1992 | Fujii et al. | | 5,547,643 A | 8/1996 | Nomoto et al. |
| 5,158,580 A | 10/1992 | Chang | | 5,549,874 A | 8/1996 | Kamiya et al. |
| D332,655 S | 1/1993 | Lytle et al. | | 5,554,344 A | 9/1996 | Duarte |
| 5,180,404 A | 1/1993 | Loreth et al. | | 5,554,345 A | 9/1996 | Kitchenman |
| 5,183,480 A | 2/1993 | Raterman et al. | | 5,565,685 A | 10/1996 | Czako et al. |
| 5,196,171 A | 3/1993 | Peltier | | 5,569,368 A | 10/1996 | Larsky et al. |
| 5,198,003 A | 3/1993 | Haynes | | 5,569,437 A | 10/1996 | Stiehl et al. |
| 5,199,257 A | 4/1993 | Colletta et al. | | D375,546 S | 11/1996 | Lee |
| 5,210,678 A | 5/1993 | Lain et al. | | 5,571,483 A | 11/1996 | Pfingstl et al. |
| 5,215,558 A | 6/1993 | Moon | | 5,573,577 A | 11/1996 | Joannou |
| 5,217,504 A | 6/1993 | Johansson | | 5,573,730 A | 11/1996 | Gillum |
| 5,217,511 A | 6/1993 | Plaks et al. | | 5,578,112 A | 11/1996 | Krause |

| | | | | | | |
|---|---|---|---|---|---|---|
| 5,578,280 | A | 11/1996 | Kazi et al. | 6,277,248 B1 | 8/2001 | Ishioka et al. |
| 5,582,632 | A | 12/1996 | Nohr et al. | 6,282,106 B2 | 8/2001 | Grass |
| 5,587,131 | A | 12/1996 | Malkin et al. | D449,097 S | 10/2001 | Smith et al. |
| D377,523 | S | 1/1997 | Marvin et al. | D449,679 S | 10/2001 | Smith et al. |
| 5,591,253 | A | 1/1997 | Altman et al. | 6,296,692 B1 | 10/2001 | Gutmann |
| 5,591,334 | A | 1/1997 | Shimizu et al. | 6,302,944 B1 | 10/2001 | Hoenig |
| 5,591,412 | A | 1/1997 | Jones et al. | 6,309,514 B1 | 10/2001 | Conrad et al. |
| 5,593,476 | A | 1/1997 | Coppom | 6,312,507 B1 | 11/2001 | Taylor et al. |
| 5,601,636 | A | 2/1997 | Glucksman | 6,315,821 B1 | 11/2001 | Pillion et al. |
| 5,603,752 | A | 2/1997 | Hara | 6,328,791 B1 | 12/2001 | Pillion et al. |
| 5,603,893 | A | 2/1997 | Gundersen et al. | 6,348,103 B1 | 2/2002 | Ahlborn et al. |
| 5,614,002 | A | 3/1997 | Chen | 6,350,417 B1 | 2/2002 | Lau et al. |
| 5,624,476 | A | 4/1997 | Eyraud | 6,362,604 B1 | 3/2002 | Cravey |
| 5,630,866 | A | 5/1997 | Gregg | 6,372,097 B1 | 4/2002 | Chen |
| 5,630,990 | A | 5/1997 | Conrad et al. | 6,373,723 B1 | 4/2002 | Wallgren et al. |
| 5,637,198 | A | 6/1997 | Breault | 6,379,427 B1 | 4/2002 | Siess |
| 5,637,279 | A | 6/1997 | Besen et al. | 6,391,259 B1 | 5/2002 | Malkin et al. |
| 5,639,294 | A * | 6/1997 | Ranstad .......................... 95/6 | 6,398,852 B1 | 6/2002 | Loreth |
| 5,641,342 | A | 6/1997 | Smith et al. | 6,447,587 B1 | 9/2002 | Pillion et al. |
| 5,641,461 | A | 6/1997 | Ferone | 6,451,266 B1 | 9/2002 | Lau et al. |
| 5,647,890 | A | 7/1997 | Yamamoto | 6,464,754 B1 | 10/2002 | Ford |
| 5,648,049 | A | 7/1997 | Jones et al. | 6,471,753 B1 | 10/2002 | Ahn et al. |
| 5,655,210 | A | 8/1997 | Gregoire et al. | 6,494,940 B1 | 12/2002 | Hak |
| 5,656,063 | A | 8/1997 | Hsu | 6,497,754 B2 | 12/2002 | Joannou |
| 5,665,147 | A | 9/1997 | Taylor et al. | 6,504,308 B1 | 1/2003 | Krichtafovitch et al. |
| 5,667,563 | A | 9/1997 | Silva, Jr. | 6,506,238 B1 | 1/2003 | Endo |
| 5,667,564 | A | 9/1997 | Weinberg | 6,508,982 B1 | 1/2003 | Shoji |
| 5,667,565 | A | 9/1997 | Gondar | 6,544,485 B1 | 4/2003 | Taylor |
| 5,667,756 | A | 9/1997 | Ho | 6,576,046 B2 | 6/2003 | Pruette et al. |
| 5,669,963 | A | 9/1997 | Horton et al. | 6,588,434 B2 | 7/2003 | Taylor et al. |
| 5,678,237 | A | 10/1997 | Powell et al. | 6,603,268 B2 | 8/2003 | Lee |
| 5,681,434 | A | 10/1997 | Eastlund | 6,613,277 B1 | 9/2003 | Monagan |
| 5,681,533 | A | 10/1997 | Hiromi | 6,632,407 B1 | 10/2003 | Lau et al. |
| 5,698,164 | A | 12/1997 | Kishioka et al. | 6,635,105 B2 | 10/2003 | Ahlborn et al. |
| 5,702,507 | A | 12/1997 | Wang | 6,635,106 B2 | 10/2003 | Katou et al. |
| D389,567 | S | 1/1998 | Gudefin | 6,672,315 B2 | 1/2004 | Taylor et al. |
| 5,766,318 | A | 6/1998 | Loreth et al. | 6,680,028 B1 | 1/2004 | Harris |
| 5,779,769 | A | 7/1998 | Jiang | 6,709,484 B2 | 3/2004 | Lau et al. |
| 5,785,631 | A | 7/1998 | Heidecke | 6,713,026 B2 | 3/2004 | Taylor et al. |
| 5,814,135 | A | 9/1998 | Weinberg | 6,735,830 B1 | 5/2004 | Merciel |
| 5,879,435 | A | 3/1999 | Satyapal et al. | 6,749,667 B2 | 6/2004 | Reeves et al. |
| 5,893,977 | A | 4/1999 | Pucci | 6,753,652 B2 | 6/2004 | Kim |
| 5,911,957 | A | 6/1999 | Khatchatrian et al. | 6,761,796 B2 | 7/2004 | Srivastava et al. |
| 5,972,076 | A | 10/1999 | Nichols et al. | 6,768,108 B2 | 7/2004 | Hirano et al. |
| 5,975,090 | A | 11/1999 | Taylor et al. | 6,768,110 B2 | 7/2004 | Alani |
| 5,980,614 | A | 11/1999 | Loreth et al. | 6,768,120 B2 | 7/2004 | Leung et al. |
| 5,993,521 | A | 11/1999 | Loreth et al. | 6,768,121 B2 | 7/2004 | Horsky et al. |
| 5,993,738 | A | 11/1999 | Goswani | 6,770,878 B2 | 8/2004 | Uhlemann et al. |
| 5,997,619 | A | 12/1999 | Knuth et al. | 6,774,359 B1 | 8/2004 | Hirabayashi et al. |
| 6,019,815 | A | 2/2000 | Satyapal et al. | 6,777,686 B2 | 8/2004 | Olson et al. |
| 6,042,637 | A | 3/2000 | Weinberg | 6,777,699 B1 | 8/2004 | Miley et al. |
| 6,063,168 | A | 5/2000 | Nichols et al. | 6,777,882 B2 | 8/2004 | Goldberg et al. |
| 6,086,657 | A | 7/2000 | Freije | 6,781,136 B1 | 8/2004 | Kato |
| 6,090,189 | A | 7/2000 | Wikström et al. | 6,785,912 B1 | 9/2004 | Julio |
| 6,117,216 | A | 9/2000 | Loreth | 6,791,814 B2 | 9/2004 | Adachi et al. |
| 6,118,645 | A | 9/2000 | Partridge | 6,794,661 B2 | 9/2004 | Tsukihara et al. |
| 6,126,722 | A | 10/2000 | Mitchell et al. | 6,797,339 B2 | 9/2004 | Akizuki et al. |
| 6,126,727 | A | 10/2000 | Lo | 6,797,964 B2 | 9/2004 | Yamashita |
| 6,149,717 | A | 11/2000 | Satyapal et al. | 6,799,068 B1 | 9/2004 | Hartmann et al. |
| 6,149,815 | A | 11/2000 | Sauter | 6,800,862 B2 | 10/2004 | Matsumoto et al. |
| 6,152,146 | A | 11/2000 | Taylor et al. | 6,803,585 B2 | 10/2004 | Glukhoy |
| 6,163,098 | A | 12/2000 | Taylor et al. | 6,805,916 B2 | 10/2004 | Cadieu |
| 6,176,977 | B1 | 1/2001 | Taylor et al. | 6,806,035 B1 | 10/2004 | Atireklapvarodom et al. |
| 6,182,461 | B1 | 2/2001 | Washburn et al. | 6,806,163 B2 | 10/2004 | Wu et al. |
| 6,182,671 | B1 | 2/2001 | Taylor et al. | 6,806,468 B2 | 10/2004 | Laiko et al. |
| 6,187,271 | B1 | 2/2001 | Lee et al. | 6,808,606 B2 | 10/2004 | Thomsen et al. |
| 6,193,852 | B1 | 2/2001 | Caracciolo et al. | 6,809,310 B2 | 10/2004 | Chen |
| 6,203,600 | B1 | 3/2001 | Loreth | 6,809,312 B1 | 10/2004 | Park et al. |
| 6,212,883 | B1 | 4/2001 | Kang | 6,809,325 B2 | 10/2004 | Dahl et al. |
| 6,228,149 | B1 | 5/2001 | Alenichev et al. | 6,812,647 B2 | 11/2004 | Cornelius |
| 6,251,171 | B1 | 6/2001 | Marra et al. | 6,815,690 B2 | 11/2004 | Veerasamy et al. |
| 6,252,012 | B1 | 6/2001 | Egitto et al. | 6,818,257 B2 | 11/2004 | Amann et al. |
| 6,270,733 | B1 | 8/2001 | Rodden | 6,818,909 B2 | 11/2004 | Murrell et al. |

| | | | | | | |
|---|---|---|---|---|---|---|
| 6,819,053 B2 | 11/2004 | Johnson | | 2007/0039462 A1* | 2/2007 | Helt et al. .................. 95/6 |
| 6,863,869 B2 | 3/2005 | Lau | | | | |
| 6,893,618 B2 | 5/2005 | Kotlyar et al. | | FOREIGN PATENT DOCUMENTS | | |
| 6,897,617 B2 | 5/2005 | Lee | | | | |
| 6,899,745 B2 | 5/2005 | Gatchell et al. | | CN | 2138764 Y | 6/1993 |
| 6,908,501 B2 | 6/2005 | Reeves et al. | | CN | 2153231 Y | 12/1993 |
| 6,958,134 B2 | 10/2005 | Taylor et al. | | DE | 2206057 | 8/1973 |
| 6,974,560 B2 | 12/2005 | Taylor et al. | | DE | 197 41 621 C1 | 6/1999 |
| 6,984,987 B2 | 1/2006 | Taylor et al. | | EP | 0433152 A1 | 12/1990 |
| 7,122,070 B1* | 10/2006 | Krichtafovitch .............. 95/2 | | EP | 0332624 B1 | 1/1992 |
| 2001/0011499 A1* | 8/2001 | Reyes ......................... 95/7 | | FR | 2690509 | 10/1993 |
| 2001/0048906 A1 | 12/2001 | Lau et al. | | GB | 643363 | 9/1950 |
| 2002/0079212 A1 | 6/2002 | Taylor et al. | | JP | 51-90077 | 8/1976 |
| 2002/0098131 A1 | 7/2002 | Taylor et al. | | JP | 62-20653 | 2/1987 |
| 2002/0122751 A1 | 9/2002 | Sinaiko et al. | | JP | 63-164948 | 10/1988 |
| 2002/0122752 A1 | 9/2002 | Taylor et al. | | JP | 10137007 | 5/1998 |
| 2002/0127156 A1 | 9/2002 | Taylor | | JP | 11104223 | 4/1999 |
| 2002/0134665 A1 | 9/2002 | Taylor et al. | | JP | 2000236914 | 9/2000 |
| 2002/0144601 A1 | 10/2002 | Palestro et al. | | WO | 92/05875 A1 | 4/1992 |
| 2002/0146356 A1 | 10/2002 | Sinaiko et al. | | WO | 96/04703 A1 | 2/1996 |
| 2002/0150520 A1 | 10/2002 | Taylor et al. | | WO | 99/07474 A1 | 2/1999 |
| 2002/0152890 A1 | 10/2002 | Leiser | | WO | WO 00/10713 A1 | 3/2000 |
| 2002/0155041 A1 | 10/2002 | McKinney, Jr. et al. | | WO | WO 01/47803 A1 | 7/2001 |
| 2002/0190658 A1 | 12/2002 | Lee | | WO | WO 01/48781 A1 | 7/2001 |
| 2002/0195951 A1 | 12/2002 | Lee | | WO | WO 01/64349 A1 | 9/2001 |
| 2003/0170150 A1 | 9/2003 | Law et al. | | WO | WO 01/85348 A2 | 11/2001 |
| 2003/0206837 A1 | 11/2003 | Taylor et al. | | WO | WO 02/20162 A2 | 3/2002 |
| 2004/0033176 A1 | 2/2004 | Lee et al. | | WO | WO 02/20163 A2 | 3/2002 |
| 2004/0096376 A1 | 5/2004 | Taylor | | WO | WO 02/30574 A1 | 4/2002 |
| 2004/0136863 A1 | 7/2004 | Yates et al. | | WO | WO 02/32578 A1 | 4/2002 |
| 2004/0166037 A1 | 8/2004 | Youdell et al. | | WO | WO 02/42003 A1 | 5/2002 |
| 2004/0226447 A1 | 11/2004 | Lau et al. | | WO | WO 02/066167 A1 | 8/2002 |
| 2004/0234431 A1 | 11/2004 | Taylor et al. | | WO | WO 03/009944 A1 | 2/2003 |
| 2004/0251124 A1 | 12/2004 | Lau | | WO | WO 03/013620 A1 | 2/2003 |
| 2005/0000793 A1 | 1/2005 | Taylor et al. | | WO | WO 03/013734 | 2/2003 |
| 2005/0051027 A1* | 3/2005 | Belson et al. ................ 95/2 | | * cited by examiner | | |

AIR TREATMENT APPARATUS HAVING A VOLTAGE CONTROL DEVICE RESPONSIVE TO CURRENT SENSING

PRIORITY CLAIM

This application claims priority to, and the benefit of, U.S. Provisional Application Ser. No. 60/777,943 entitled "FEEDBACK CONTROL SYSTEMS AND METHODS FOR AN ELECTROSTATIC PRECIPITATOR," filed on Feb. 28, 2006.

CROSS-REFERENCE TO RELATED APPLICATIONS

This application relates to the following co-owned and co-pending applications: U.S. Pat. No. 6,984,987, issued on Jan. 10, 2006; U.S. patent application Ser. No. 90/007,276, filed Oct. 29, 2004; U.S. patent application Ser. No. 11/041,926, filed Jan. 21, 2005; U.S. Pat. No. 7,285,155, issued Oct. 23, 2007; U.S. patent application Ser. No. 10/978,891, filed Nov. 1, 2004 (now abandoned); U.S. Pat. No. 7,381,381, issued Jun. 3, 2008; U.S. patent application Ser. No. 11/062,057, filed Feb. 18, 2005 (now abandoned); U.S. patent application Ser. No. 11/003,516, filed Dec. 3, 2004 (now abandoned); U.S. patent application Ser. No. 11/071,779, filed Mar. 3, 2005; U.S. patent application Ser. No. 10/994,869, filed Nov. 22, 2004; U.S. Pat. No. 7,291,207, issued 2001 Nov. 6, 2007; U.S. patent application Ser. No. 11/003,894, filed Dec. 3, 2004 (now abandoned); U.S. Pat. No. 7,638,104, issued Dec. 29, 2009; U.S. Pat. No. 7,517,503, issued Apr. 14, 2009; U.S. patent application Ser. No. 11/006,344, filed Dec. 7, 2004 (now abandoned; U.S. Pat. No. 7,695,690, issued Apr. 13, 2010; U.S. patent application Ser. No. 10/023,460, filed Dec. 13, 2001 (now abandoned); U.S. patent application Ser. No. 10/379,966, filed Mar. 5, 2003 (now abandoned); U.S. Pat. No. 7,404,935, issued Jul. 29, 2008; U.S. patent application Ser. No. 10/944,016, filed Sep. 17, 2004; U.S. Pat. No. 7,517,504, issued Apr. 14, 2009; U.S. patent application Ser. No. 10/435,289, filed May 9, 2003; U.S. patent application Ser. No. 11/064,797, filed Feb. 24, 2005 (now abandoned); U.S. patent application Ser. No. 11/003,034, filed Dec. 3, 2004 (now abandoned); U.S. Pat. No. 7,517,505, issued Apr. 14, 2009; U.S. patent application Ser. No. 11/003,671, filed Dec. 3, 2004 now abandoned); U.S. Pat. No. 7,318,856, issued Jan. 15, 2008; U.S. patent application Ser. No. 11/007,395, filed Dec. 8, 2004; U.S. patent application Ser. No. 10/074,827, filed Feb. 12, 2002 (now abandoned); U.S. patent application Ser. No. 10/876,495, filed Jun. 25, 2004 (now abandoned); U.S. Pat. No. 7,405,672, issued Jul. 29, 2008; U.S. patent application Ser. No. 11/062,173, filed Feb. 18, 2005 (now abandoned); U.S. patent application Ser. No. 11/004,397, filed Dec. 3, 2004; U.S. patent application Ser. No. 10/895,799, filed Jul. 21, 2004 (now abandoned); U.S. patent application Ser. No. 10/642,927, filed Aug. 18, 2003 (now abandoned); U.S. patent application Ser. No. 11/823,346, filed Apr. 12, 2004; U.S. Pat. No. 7,371,354, issued May 13, 2008; U.S. patent application Ser. No. 11/061,967, filed Feb. 18, 2005; U.S. Pat. No. 7,662,348, issued Feb. 16, 2010; U.S. patent application Ser. No. 11/188,448, filed Jul. 25, 2005; U.S. Pat. No. 7,311,762, issued Dec. 25, 2007; U.S. Provisional Application No. 60/777,943, filed Feb. 25, 2006; U.S. patent application Ser. No. 11/293,538, filed Dec. 2, 2005; U.S. patent application Ser. No. 11/338,974, filed Jan. 25, 2006; U.S. Pat. No. 6,899,745, issued May 31, 2005; U.S. patent application Ser. No. 11/457,396, filed Jul. 13, 2006; and U.S. patent application Ser. No. 11/464,139, filed Aug. 11, 2006.

INCORPORATION BY REFERENCE

The contents of the following patent applications and issued patents are fully incorporated herein by reference: U.S. patent application Ser. No. 90/007,276, filed Oct. 29, 2004; U.S. patent application Ser. No. 09/419,720, filed Oct. 14, 1999, now U.S. Pat. No. 6,504,308; U.S. patent application Ser. No. 11/041,926, filed Jan. 21, 2005; U.S. patent application Ser. No. 09/231,917, filed Jan. 14, 1999, now U.S. Pat. No. 6,125,636; U.S. patent application Ser. No. 11/091,243, filed Mar. 28, 2005, now U.S. Pat. No. 7,285,155; U.S. patent application Ser. No. 10/978,891, filed Nov. 1, 2004 (now abandoned); U.S. patent application Ser. No. 11/087,969, filed Mar. 23, 2005, now U.S. Pat. No. 7,056,370; U.S. patent application Ser. No. 09/197,131 filed Nov. 20, 1998, now U.S. Pat. No. 6,585,935; U.S. patent application Ser. No. 08/924,580, filed Sep. 5, 1997, now U.S. Pat. No. 5,802,865; U.S. patent application Ser. No. 09/148,843, filed Sep. 4, 1998, now U.S. Pat. No. 6,189,327; U.S. patent application Ser. No. 09/232,196, filed Jan. 14, 1999, now U.S. Pat. No. 6,163,098; U.S. patent application Ser. No. 10/454,132, filed Jun. 4, 2003, now U.S. Pat. No. 6,827,088; U.S. patent application Ser. No. 09/721,055, filed Nov. 22, 2000, now U.S. Pat. No. 6,640,049; U.S. patent application Ser. No. 10/405,193, filed Apr. 1, 2003, now U.S. Pat. No. 7,381,381; U.S. patent application Ser. No. 09/669,253, filed Sep. 25, 2000, now U.S. Pat. No. 6,632,407; U.S. patent application Ser. No. 09/249,375, filed Feb. 12, 1999, now U.S. Pat. No. 6,312,507; U.S. patent application Ser. No. 09/742,814, filed Dec. 19, 2000, now U.S. Pat. No. 6,672,315; U.S. patent application Ser. No. 09/415,576, filed Oct. 8, 1999, now U.S. Pat. No. 6,182,671; U.S. patent application Ser. No. 09/344,516, filed Jun. 25, 1999, now U.S. Pat. No. 6,152,146; U.S. patent application Ser. No. 09/163,024, filed Sep. 29, 1998, now U.S. Pat. No. 5,975,090; U.S. patent application Ser. No. 11/062,057, filed Feb. 18, 2005 (now abandoned); U.S. patent application Ser. No. 10/188,668, filed Jul. 2, 2002, now U.S. Pat. No. 6,588,434; U.S. patent application Ser. No. 10/815,230, filed Mar. 30, 2004, now U.S. Pat. No. 6,953,556; U.S. patent application Ser. No. 11/003,516, filed Dec. 3, 2004 (now abandoned); U.S. patent application Ser. No. 11/071,779, filed Mar. 3, 2005; U.S. patent application Ser. No. 10/994,869, filed Nov. 22, 2004; U.S. patent application Ser. No. 11/007,556, filed Dec. 8, 2004, now U.S. Pat. No. 7,291,207; U.S. patent application Ser. No. 11/003,894, filed Dec. 3, 2004 (now abandoned); U.S. patent application Ser. No. 10/661,988, filed Sep. 12, 2003, now U.S. Pat. No. 7,097,695; U.S. patent application Ser. No. 10/774,579, filed Feb. 9, 2004, now U.S. Pat. No. 7,077,890; U.S. patent application Ser. No. 09/730,499, filed Dec. 5, 2000, now U.S. Pat. No. 6,713,026; U.S. patent application Ser. No. 10/156,158, filed May 28, 2002, now U.S. Pat. No. 6,863,869; U.S. patent application Ser. No. 09/186,471, filed Nov. 5, 1998, now U.S. Pat. No. 6,176,977; U.S. patent application Ser. No. 11/003,752, filed Dec. 3, 2004, now U.S. Pat. No. 7,638,104; U.S. patent application Ser. No. 10/835,743, filed Apr. 30, 2004, now U.S. Pat. No. 6,908,501; U.S. patent application Ser. No. 10/791,561, filed Mar. 2, 2004, now U.S. Pat. No. 7,571,503; U.S. patent application Ser. No. 10/658,721, filed Sep. 9, 2003, now U.S. Pat. No. 6,896,853; U.S. patent application Ser. No. 11/006,344, filed Dec. 7, 2004 (now abandoned); U.S. patent application Ser. No. 10/074,209, filed Feb. 12, 2002, now U.S. Pat. No. 7,695,690; U.S. patent application Ser. No. 10/023,460, filed Dec. 13, 2001 (now abandoned); U.S. patent application Ser. No. 10/379,966, filed Mar. 5, 2003 (now abandoned); U.S. patent application Ser. No. 10/685,182, filed Oct. 14, 2003; U.S. patent application Ser. No. 10/944,016, filed Sep. 17, 2004; U.S. patent application Ser. No. 10/074,096, filed Feb. 12, 2002, now U.S. Pat. No. 6,974,560; U.S. patent application Ser. No. 10/074,347, filed Feb. 12, 2002, now U.S. Pat. No. 6,911,186; U.S. patent application Ser. No. 10/795,934, filed Mar. 8, 2004, now U.S. Pat. No. 7,517,504; U.S. patent application Ser. No. 10/435,289, filed May 9, 2003; U.S. patent application Ser. No. 09/774,198, filed Jan. 29, 2001, now U.S. Pat. No. 6,544,485; U.S. patent application Ser. No. 11/064,797, filed Feb. 24, 2005 (now abandoned); U.S. patent application Ser. No. 11/003,034, filed Dec. 3, 2004 (now abandoned); U.S. patent application Ser. No. 11/007,734, filed Dec. 8, 2004, now U.S. Pat. No. 7,517,505; U.S. patent application Ser. No. 11/003,671, filed Dec. 3, 2004 (now abandoned); U.S. patent application Ser. No. 11/003,035, filed Dec. 3, 2004, now U.S. Pat. No. 7,318,856; U.S. patent application Ser. No. 11/007,395, filed Dec. 8, 2004; U.S. patent application Ser. No. 10/074,827, filed Feb. 12, 2002 (now abandoned); U.S. patent application Ser. No. 10/876,495, filed Jun. 25, 2004 (now abandoned); U.S. patent application Ser. No. 10/809,923, filed Mar. 25, 2004, now U.S. Pat. No. 7,405,672; U.S. patent application Ser. No. 11/062,173, filed Feb. 18, 2005 (now abandoned); U.S. patent application Ser. No. 10/074,082, filed Feb. 12, 2002, now U.S. Pat. No. 6,958,134; U.S. patent application Ser. No. 10/278,193, filed Oct. 21, 2002, now U.S. Pat. No. 6,749,667; U.S. patent application Ser. No. 09/924,600, filed Aug. 8, 2001, now U.S. Pat. No. 6,709,484; U.S. patent application Ser. No. 09/564,960, filed May 4, 2000, now U.S. Pat. No. 6,350,417; U.S. patent application Ser. No. 10/806,293, filed Mar. 22, 2004, now U.S. Pat. No. 6,972,057; U.S. patent application Ser. No. 11/004,397, filed Dec. 3, 2004; U.S. patent application Ser. No. 10/895,799, filed Jul. 21, 2004 (now abandoned); U.S. patent application Ser. No. 10/625,401, filed Jul. 23, 2003, now U.S. Pat. No. 6,984,987; U.S. patent application Ser. No. 10/642,927, filed Aug. 18, 2003 (now abandoned); U.S. patent application Ser. No. 11/823,346, filed Apr. 12, 2004; U.S. patent application Ser. No. 10/662,591, filed Sep. 15, 2003, now U.S. Pat. No. 7,371,354; U.S. patent application Ser. No. 11/061,967, filed Feb. 18, 2005; U.S. patent application Ser. No. 11/150,046, filed Jun. 10, 2005, now U.S. Pat. No. 7,662,348; U.S. patent application Ser. No. 11/188,448, filed Jul. 25, 2005; U.S. patent' application Ser. No. 11/188,478, filed Jul. 25, 2005; U.S. Provisional Application No. 60/777,943, filed Feb. 25, 2006; U.S. patent application Ser. No. 11/293,538, filed Dec. 2, 2005, now U.S. Pat. No. 7,311,762; U.S. patent application Ser. No. 11/338,974, filed Jan. 25, 2006; U.S. patent application Ser. No. 10/794,526, filed Mar. 4, 2004, now U.S. Pat. No. 7,014,686; U.S. patent application Ser. No. 11/457,396, filed Jul. 13, 2006; U.S. patent application Ser. No. 11/464,139, filed Aug. 11, 2006; U.S. patent application Ser. No. 10/168,723, filed Jun. 21, 2002, now U.S. Pat. No. 6,897,617; and U.S. patent application Ser. No. 10/168,724, filed Jun. 21, 2002, now U.S. Pat. No. 6,603,268.

COPYRIGHT NOTICE

A portion of the disclosure of this patent document contains material which is subject to copyright protection. The copyright owner has no objection to the photocopy reproduction by anyone of the patent document or the patent disclosure in exactly the form it appears in the Patent and Trademark Office patent file or records, but otherwise reserves all copyright rights whatsoever.

BACKGROUND

Ionic air cleaners clean air by electrically charging particles in the air, such as dust, and then collecting the charged particles within the cleaner. However, effective air cleaning of such ionic cleaners can depend, at least in part, on adequate voltage control. Known ionic air cleaners can have relatively high deviations in voltage during the operation of the cleaner. Conventional voltage control techniques include automatic voltage control (AVC) which monitors the voltage for controlling operation of the device. However, AVC can have its drawbacks because relatively small changes in voltage can lead to relatively large changes in current. Relatively large changes in current can decrease operational efficiency and decrease control over the creation of by-products, such as ozone. Therefore, there is a need to overcome such disadvantages or otherwise lessen the effects of such disadvantages.

SUMMARY

The air treatment apparatus, in one embodiment, includes a housing which supports: (a) an electrode assembly; (b) a voltage supply providing power to the electrode assembly; (c) a current sensing device operably coupled to the electrode assembly; and (d) a voltage control device coupled to the current sensing device and the voltage supply. The voltage control device is configured to dynamically determine (e.g., measure) a level of current flowing through the current sensing device. This current is representative of the current flowing in the electrode assembly. The voltage control device uses this measurement of current to regulate the level of voltage generated by the voltage supply.

There is a relationship between current and voltage in the electrode assembly such that as the voltage fluctuates, the current fluctuates. However, relatively small changes in voltage result in relatively large changes in current. The current sensing device provides current data or signals which facilitate the early detection of voltage and current in the electrode assembly that is deviating, or moving away from, one or more designated operating ranges. As a result, these current signals received from the current sensing device enable the voltage control device to dynamically steer or redirect the voltage and current levels in the electrode assembly toward these one or more designated operating ranges. In one embodiment, the designated operating ranges are associated with the optimum operating efficiency of the air treatment apparatus, and with more desirable ozone production levels.

Other features and advantages of the invention will be apparent from the following detailed disclosure, taken in conjunction with the accompanying sheets of drawings, wherein like numerals refer to like parts, elements, components, steps and processes.

DETAILED DESCRIPTION

General Electronic Configuration

Figure 1:
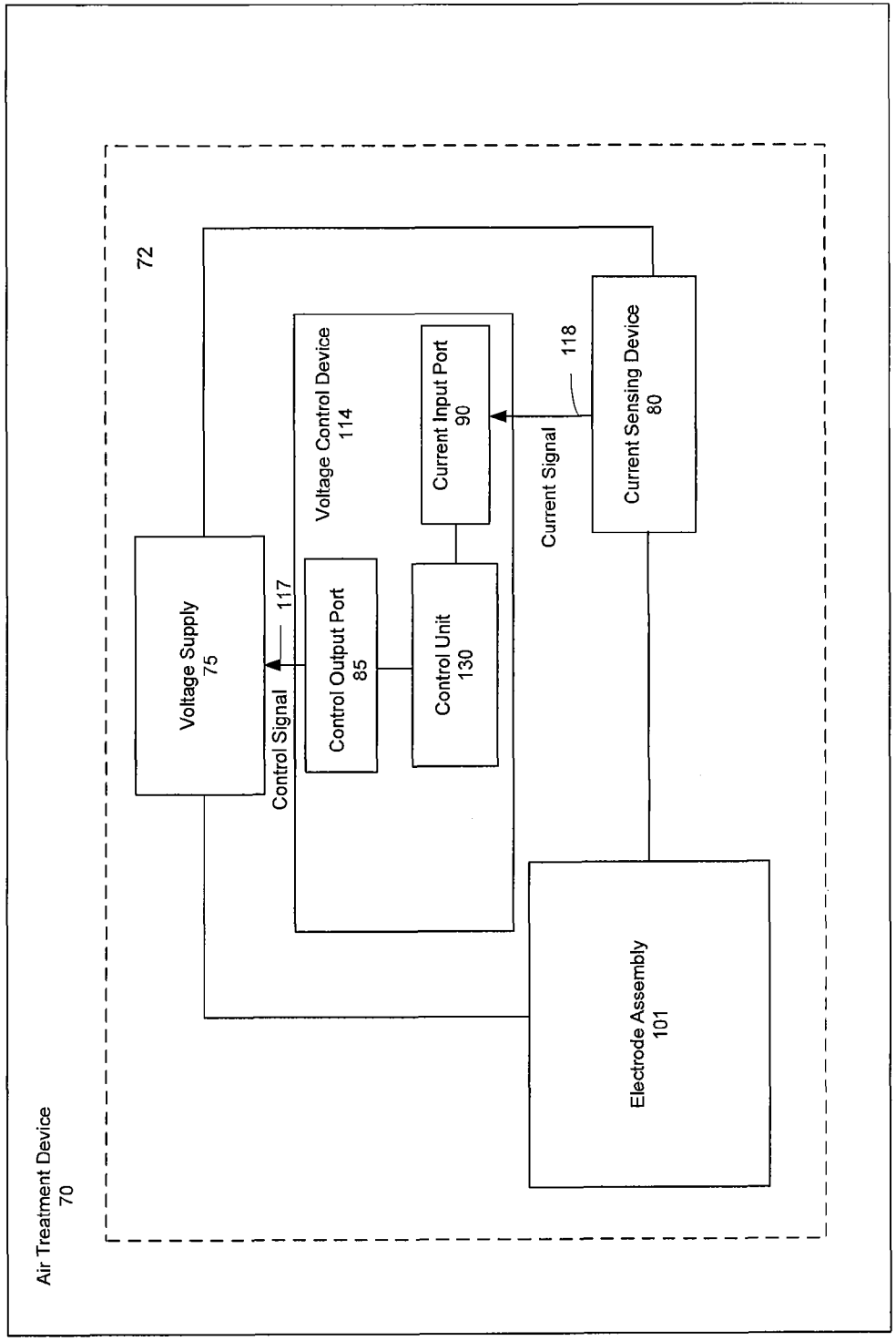
FIG. 1 is a schematic diagram of one embodiment of an air treatment apparatus with voltage control.

Referring to FIG. 1, in one embodiment, the air treatment apparatus 70 includes a housing (described below with reference to FIGS. 9-10) and a voltage control circuit 72 supported by the housing. The voltage control circuit 72 includes an electrode assembly 101, a voltage supplier 75, one or more current sensing devices 80 and a voltage control device 114. The electrode assembly 101 includes an electrode array (not shown) that receives voltage from the voltage supplier 75, which is an alternating current (AC) voltage supply. The voltage supplier 75 provides sufficient voltage to achieve ion emission and corona discharge in the electrode assembly 101.

In one embodiment of the air treatment apparatus 70, the voltage supplier 75 provides voltage to the electrode assembly 101 such that an electric field is established between at least one emitter electrode and at least one collector electrode (i.e., electrode array) in the electrode assembly 101. The voltage supplied by the voltage supplier 75 to the electrode assembly 101 causes current flowing at the emitter to create a corona region around the emitter electrode. This corona region has a sufficient electric field to ionize air molecules flowing in the region (i.e., generate ions). The electrical discharge associated with the ionization process is sometimes referred to as corona discharge. Thus, the generated ions create corona discharge around the emitter electrode. The operation of one embodiment of the electrode assembly 101 and the electrode array is described in more detail below with reference to FIG. 4.

As illustrated in FIG. 1, the electrode assembly 101 is also operably coupled to one or more current sensing devices 80. The current sensing device 80 includes any suitable electrical device from which current can be measured such as a resistor, an inductor, a Hall-effect element, a magnetoresistive (MR) sensor, a current transformer, or other suitable electrical device. The current flowing through the current sensing device 80 is substantially equal to or otherwise representative of the current flowing through the electrode assembly 101. Thus, the voltage control device 114 is configured to determine (e.g., measure) the current flowing through the current sensing device 80 and control the voltage supplier 75 based on the determined (e.g., measured) current.

The voltage control device 114, in one embodiment, includes a control unit 130, a current input port 90 and a control output port 85. The control unit 130 can be a proportional-integral controller, a proportional-integral-derivative controller, a fuzzy logic controller, a solid state controller, a logic engine, digital or analog controller or any other suitable combination of discrete electrical components. The current input port 90 receives a current signal 118 from the current sensing device 80 and provides current information or data in the current signal 118 to the control unit 130. The control unit 130 is configured to determine a current value from the current information or data in the current signal 118, and provide an appropriate control signal 117 for adjusting the voltage supplier 75 via the control output port 85. Adjusting the voltage supplier 75 in this manner in turn changes the operating current and voltage in the electrode assembly 101.

Figure 2:
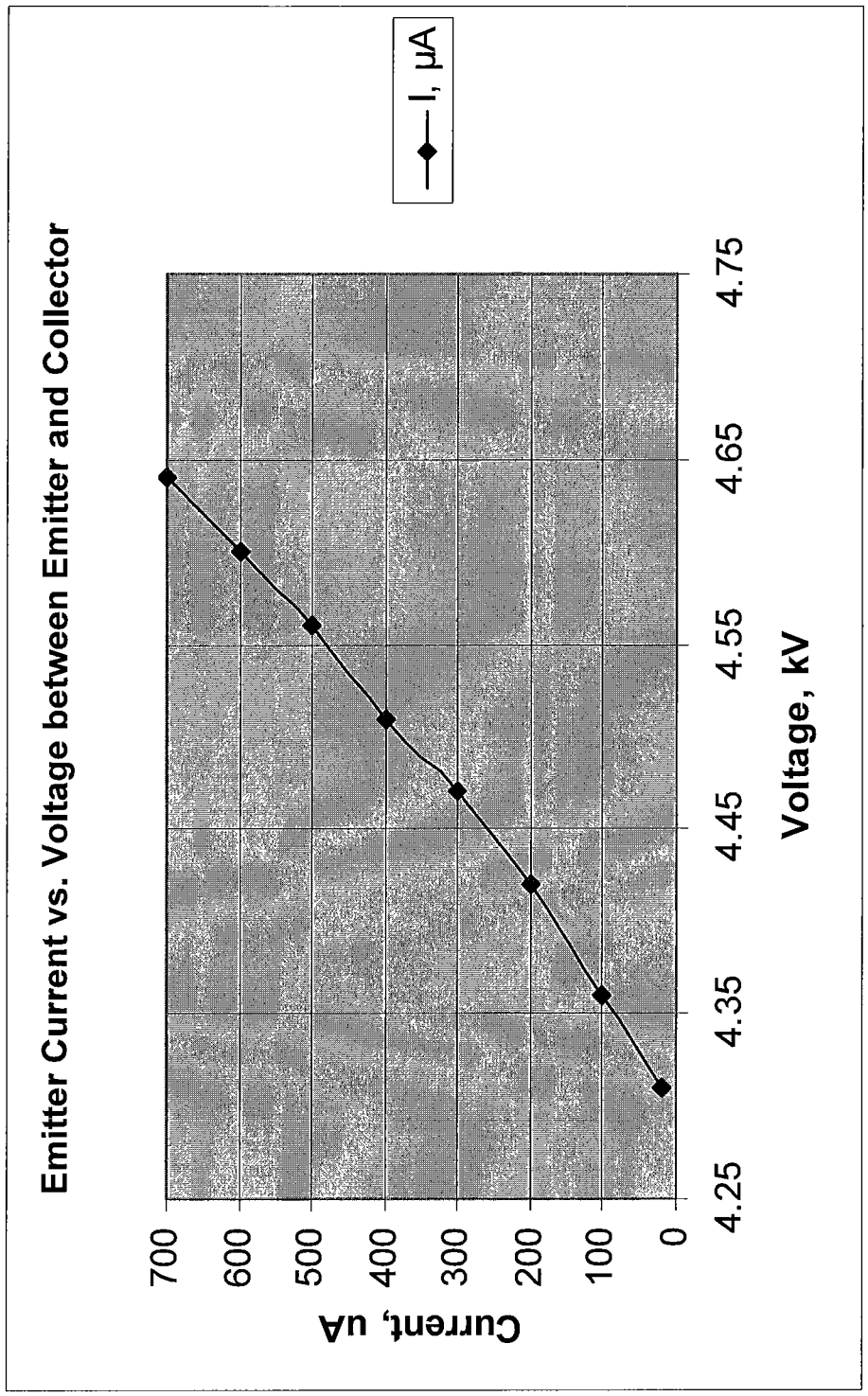
FIG. 2 is a flow chart illustrating corona current versus voltage in an electrode assembly of an air treatment apparatus.

An advantage of using current sensing to control the voltage supplier 75 is that it provides a higher degree of incremental control over the current and voltage in the electrode assembly 101. This is due to the relationship between voltage and current in the electrode assembly. The relationship between current and voltage in the electrode assembly is illustrated by the example shown in FIG. 2. At the left side of the graph, the plotted line begins (i.e., between 4.25 kV and 4.35 kV) at the point at which corona discharge is achieved (i.e., corona threshold) around the ion emitting electrode (i.e., emitter) of the electrode assembly 101. As illustrated in FIG. 2, the corona discharge is achieved at approximately 4.3 kV, which is the voltage (i.e., inception voltage) required to create a current (e.g., µA) at the ion emitting electrode of the electrode assembly sufficient to charge or ionize surrounding air molecules. When the voltage potential in the electrode assembly is below the threshold of 4.3 kV, the voltage is insufficient to produce ions or corona discharge.

As shown in FIG. 2, once ion emission and corona discharge is achieved, the current in the electrode assembly increases as a function of the increase in voltage. The graph illustrates that relatively small increases or changes in the voltage (e.g., 4.35-4.45 kV or ≈2%) result in relatively large increases or changes in the current (e.g., 80-250 µA or ≈200%). It should be understood that the data illustrated in FIG. 2 is exemplary, and ion emission and corona discharge will vary depending on the configuration of the air treatment apparatus such as airflow, and power or size requirements.

Figure 3:
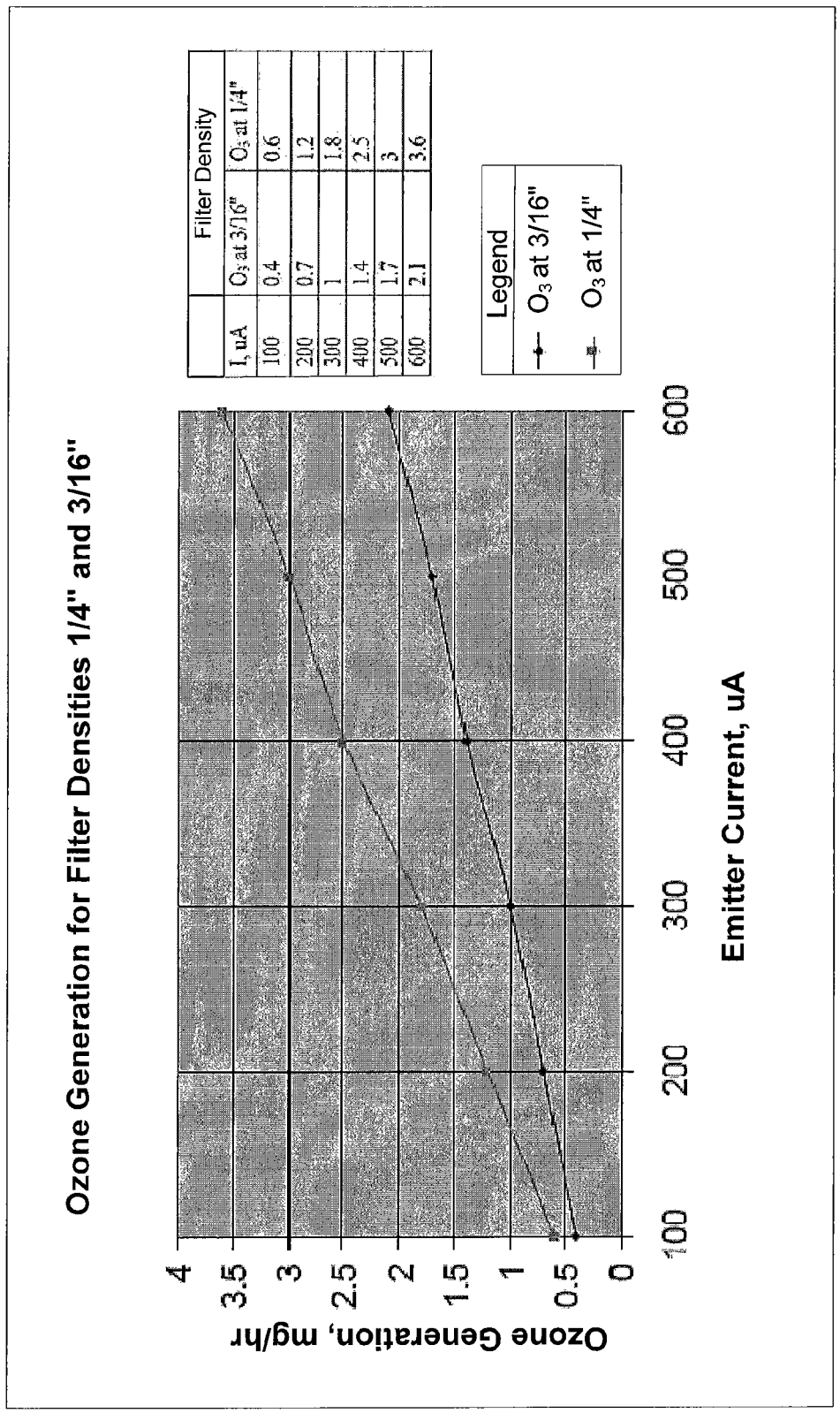
FIG. 3 is a flow chart illustrating ozone generation versus emitter current in an electrode assembly of an air treatment apparatus.

In one embodiment, voltage control of the air treatment apparatus is implemented to regulate ozone production. It should be understood that various chemical and physical factors can result in ozone production which include, but are not limited to, ozone production due to corona discharge. FIG. 3 illustrates the relationship between ozone ($O_3$) production versus emitter current in the electrode assembly 101. In one embodiment, ozone generation is due, at least in part, to corona discharge in the electrode assembly. As noted in the discussion of FIG. 2, ion emission results in corona discharge. This ionization process can cause oxygen molecules ($O_2$) to split in the air. The split molecules can seek stability and attach themselves to other oxygen molecules ($O_2$), forming ozone ($O_3$).

As illustrated in FIG. 3, an ozone mitigation device (not shown) can include multiple ozone filters, such as a honeycomb structure with cell sizes ¼" and ³⁄₁₆". It should be understood that the ozone mitigation device can be part of, or separate from, the air treatment apparatus 70. The graph in FIG. 3 illustrates one example in which ozone production increases (e.g., 0-4 mg/hr) as current increases (100-600 uA) in the electrode assembly 101. In one embodiment, there can be one or more designated ranges of ozone or ozone production including, but not limited to, the ozone production ranges set forth along the y-axis in FIG. 3. The voltage control device 114, as coupled to the current sensing device 18, enables control of ozone within those designated ranges. In one example of one embodiment, the designated ozone ranges (as shown below in Table 1) correlate to: (a) ozone production by the air cleaning apparatus 70 when having various operating settings (e.g., quiet, low, med, high and boost); and (b) current in the electrode assembly 101 within the ranges (e.g., 100-600 uA) illustrated in FIG. 3.

TABLE 1

| Settings | $O_3$, mg/hr |
|---|---|
| Quiet | 1.8 |
| Low | 2.1 |
| Med | 2.7 |
| High | 3.5 |
| Boost | 4.2 |

Ozone production by the air treatment apparatus 70 can have advantages or disadvantages depending upon the percentage of ozone in the air and other factors. The enhanced voltage control of the voltage control device 114 results in improved control over emitter current which, in turn, results in enhanced control over ozone production.

Circuitry Embodiments

Figure 4:
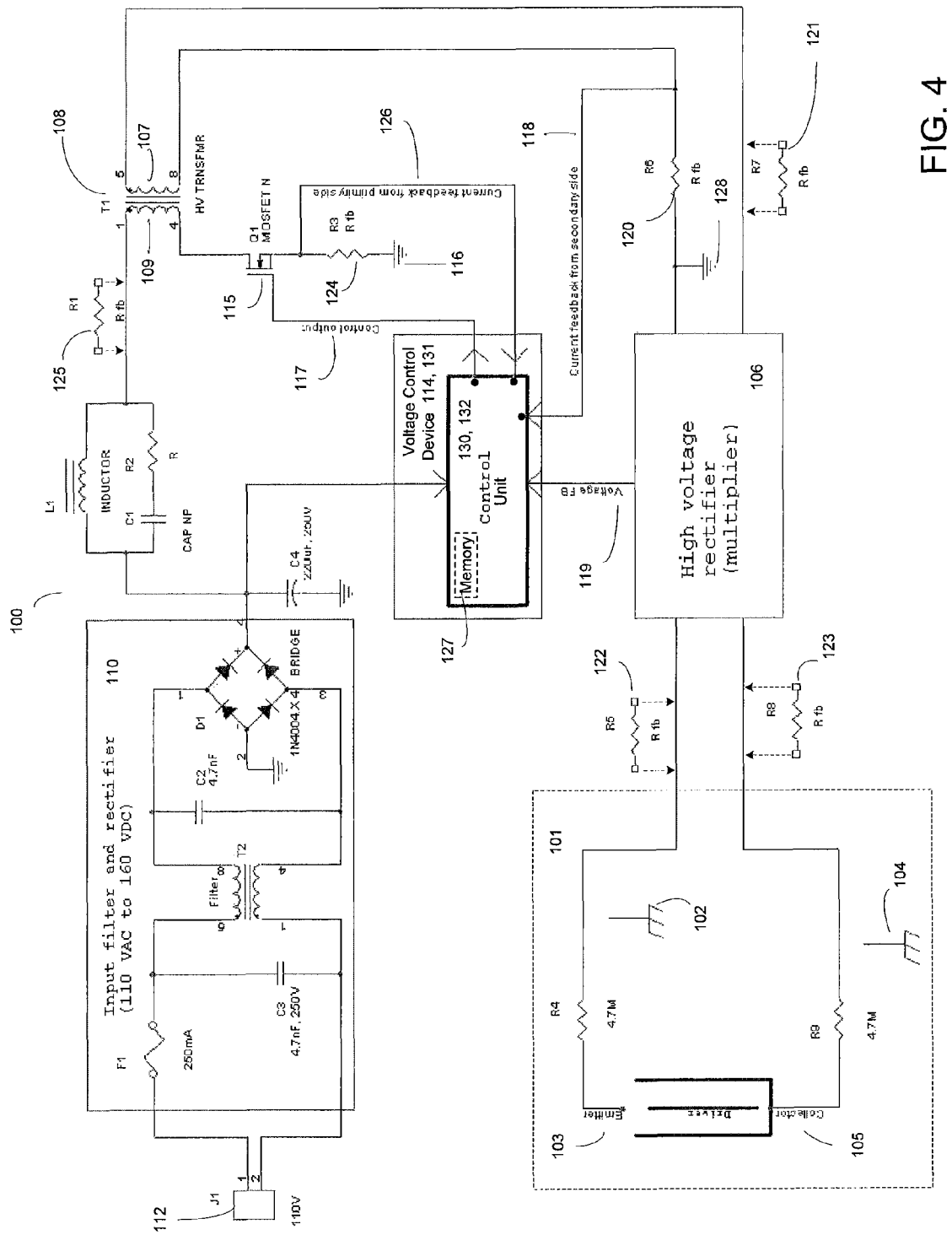
FIG. 4 is a detailed schematic diagram of one embodiment of an air treatment apparatus that includes voltage control circuitry with current sensing.

In one embodiment illustrated in FIG. 4, the air treatment apparatus 70 includes the circuit 100. The circuit 100 includes an electrode assembly 101 that receives sufficient voltage to produce an electric field between one or more emitters 103 and one or more collectors 105. The electric field intensity at the emitter 103 is sufficient to ionizes air molecules flowing near the emitter, which creates corona discharge. The ions generated by the emitter collide with and charge dust particles flowing through the electrode assembly 101. The ions and the charged particles (e.g., positive) of dust accelerate downstream toward the oppositely charged (e.g., negative) collector 105, and collect on a collection plate (not shown) of the collector 105. Also, accelerating ions can push air molecules creating ion wind or electrostatic propulsion in a downstream direction toward the collector. It should be understood that any suitable alternate polarity between the emitter and collector is usable, and the polarity of the emitter and collector is sufficient to produce an electric field which encourages the acceleration of ions and dust particles from the emitter to the collector.

In one embodiment illustrated in FIG. 4, the voltage supplier 75 includes a high voltage rectifier or multiplier 106 (e.g., a voltage doubler, quad, etc.), which provides voltage to the electrode assembly 101. Either the emitter 103 or the collector 105 of the electrode assembly 101 can be coupled to ground 102, 104 or coupled to a high voltage potential. The high voltage rectifier 106 is at any potential, grounded or ungrounded, as long as the voltage provided to the electrode assembly 101 is sufficient to create ion generation from the emitter 103. The high voltage rectifier 106 is coupled to the secondary winding 107 of the transformer 108, and the voltage from the secondary 107 is a high alternating current (AC) voltage. The AC component of the primary winding 109 voltage is stepped up by transformer 108 to provide the high AC voltage on the secondary winding 107.

The rectifier section of the input filter and rectifier unit 110 supplies voltage to the primary winding 109 of the transformer 108. The input filter and rectifier unit 110 receives AC voltage (e.g., 110 VAC) from, for example, a wall outlet 112. The primary winding 109 of the transformer 108 is connected in series with a switch 115 (e.g., a MOSFET), which in turn is operated by a voltage control device 131. The operation of the switch 115 regulates the voltage at the primary winding 109 of the transformer 108. More specifically, the voltage control device 131 pulses (i.e., turns on and off) the switch 115 under certain operating conditions, which regulates the voltage at the primary winding 109 of the transformer 108. Changes in voltage at primary winding 109 of the transformer translate into changes in emitter current.

The regulation of the voltage at the primary winding 109 of the transformer 108 is based on a control signal 118, 126 received from at least one current sensing device 80. By way of example, in FIG. 2, the current sensing device 80, which in one embodiment is a resistor, includes any one or any suitable combination of the following devices: 120, 121, 122, 123, 124, and 125. Several different circuit configurations for placement of a device 120, 121, 122, 123, 124, 125 are possible. In one embodiment, a resistor device 120 is connected in series with the secondary winding 107 of the transformer 108, and also connected to ground potential 128. The current flowing through the resistor device 120 is the current flowing though the secondary winding 107 of the transformer 108, which is substantially equal to or otherwise proportional to current flowing in the emitter 103 of the electrode assembly 101. The voltage control device 131 includes a control unit 132 that receives a current input signal 118 based on the current flowing through the resistor device 120. The control unit 132 processes the current data or information provided by the current input signal 118, determines a current value, and controls the operation of the switch 115. The operation of the switch 115, in turn, regulates the voltage at the primary winding 109 of the transformer 108, which, in turn, changes the current and voltage in the emitter 103 of the electrode assembly 101.

In another embodiment, a resistor device 121 is connected in series with the secondary winding 107; but instead of being grounded, it is configured to be under a high voltage potential. In this case, the current flowing through the resistor device 121 reflects a current level substantially equal or otherwise proportional to the current in the emitter 103 of the electrode assembly 101. The control unit 132 receives a current signal based on the current flowing through the resistor device 121, and regulates the voltage at the primary winding 109 of the transformer 108. Regulating the voltage at the primary winding 109 of the transformer 108 adjusts the operating voltage and current load in the electrode assembly 101. It should be understood that the location of the current signal 118, 126 will vary depending on the location of the current sensing device 80, and FIG. 4 does not illustrate every possibility configuration of the current signal circuitry contemplated.

In another embodiment, a resistor device 122, 123 is connected in series with the electrode assembly 101 and also connects to ground 102, 104. In this case, the current flowing through the resistor device 122, 123 is substantially equal to the current flowing in the emitter 103 of the electrode assembly 101. The control unit 132 receives a current control signal 118, 126 based on the current flowing through the resistor device 122, 123, and regulates the voltage at the primary winding 109 of the transformer 108. In another embodiment, a resistor device 124 is connected in series with the primary winding 109 of the transformer 108. In this configuration, it is assumed that the transformer 108 is not in a saturation condition. The current flowing through the primary winding 109 has a designated proportional relationship with the current flowing through the secondary winding 107 of the transformer 108; depending on the configuration of the transformer 108. Thus, the current flowing through the primary winding 109 can be used to determine the current flowing through the secondary winding 107. As noted previously, the current flowing through the secondary winding 107 of the transformer 108 is substantially equal or otherwise proportional to the current flowing in the emitter 103 of the electrode assembly 101.

Again, the control unit 132 receives a current control signal 126 based on the current flowing through the resistor device 123, 124 and regulates the voltage at the primary winding 109 of the transformer 108. In yet another embodiment, a current sensing device 125 is connected in series with the primary winding 109 of the transformer 109, wherein the resistor 125 is under high voltage potential, as opposed to being grounded. Again, the current measured at the resistor device 124, 125 is suitable for regulating the voltage at the primary winding 109 of the transformer 108.

The embodiments described above include a resistor device as the current sensing device. However, the current sensing device can be an inductor, a Hall-effect element, a magnetoresistive (MR) sensor, a current transformer, or any suitable electrical device from which current can be measured, including an electrical device that wraps around a conductor to measure current.

Additionally, control unit 132 can be a proportional-integral controller, a proportional-integral-derivative controller, a fuzzy logic controller, a solid state controller, a programmable logic controller, a logic engine, digital or analog controller, or any other suitable combination of discrete electrical components. In one embodiment, the control unit 132 includes a memory 127 that is configured to store machine readable executable instructions or control routines that are executable by the control unit 132. The instruction or control routines cause the control unit 132 to regulate the operation of the switch 115. In operation, the control unit 132 dynamically receives current data or information via the current control signal 118, 126, processes the current data or information based on the control routines to determine a current value, and responsively regulates the voltage supplied to electrode assembly 101.

Figure 5:
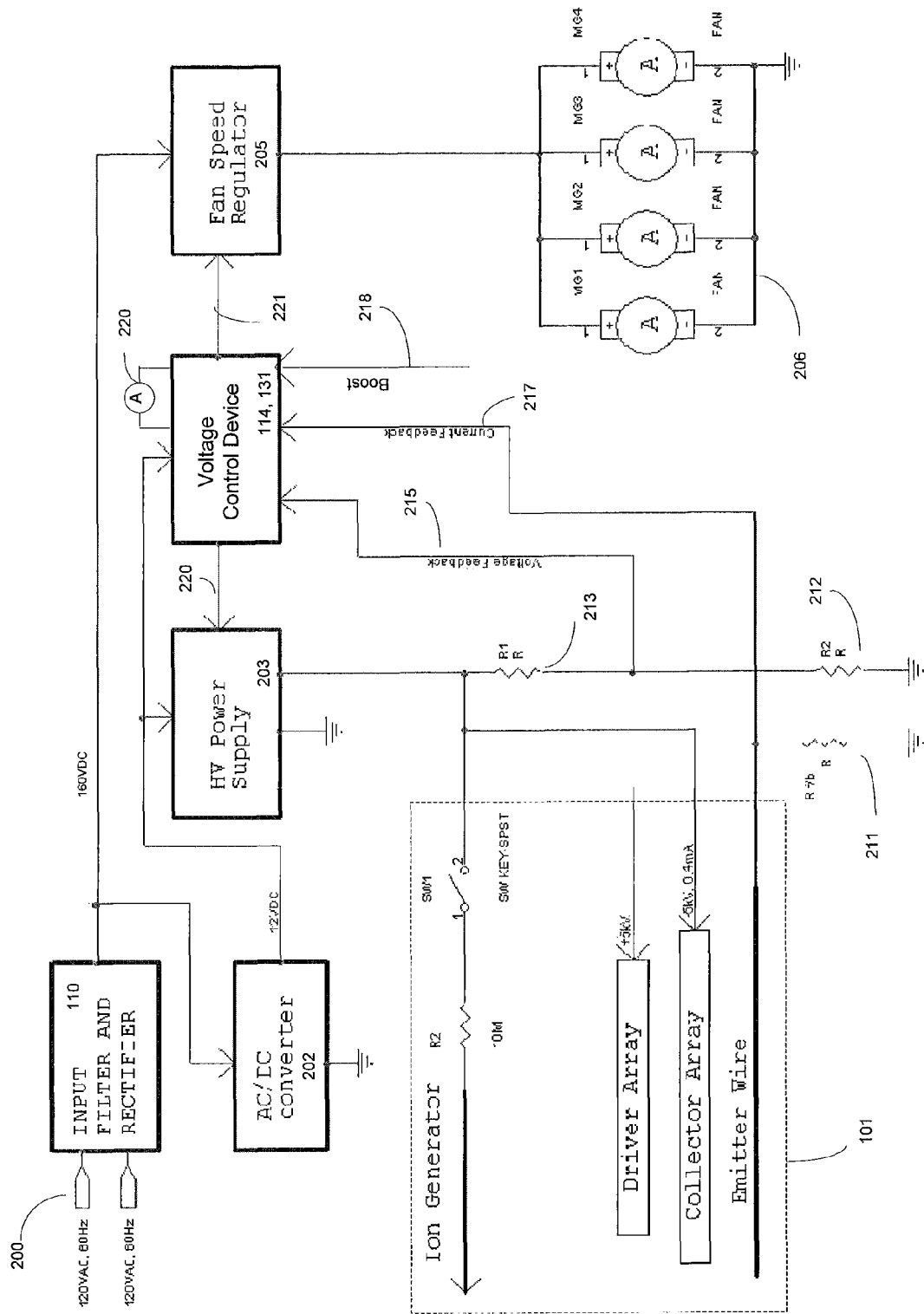
FIG. 5 is a detailed schematic diagram of one embodiment of an air treatment apparatus that includes voltage sensing circuitry.

FIG. 5 is a schematic diagram illustrating one embodiment for an electric circuit for an air treatment apparatus 70 that includes voltage sensing circuitry. Similar to FIG. 4, FIG. 5 illustrates an electrode assembly 101 and current sensing circuitry (i.e., 211, 217) of one embodiment of the air treatment apparatus 70. The operation of the electrode assembly 101 and the current sensing circuitry 211, 217 are similar to that already described in FIG. 4; thus, operation of these components will not be discussed. However, the circuitry of FIG. 4 differs from that of FIG. 5 in that it includes a voltage sensing signal 215, a fan speed regulator 205 and a plurality of fans 206.

As illustrated in FIG. 5, the electrode assembly 101 receives power from the high voltage power supply 203. Similar to the circuitry illustrated in FIG. 4, the high voltage power supply 203 includes a high voltage transformer and a voltage multiplier circuit (not shown). The input filter and rectifier 110 and the AC/DC converter 202 are coupled to the high voltage power supply 203, and an external AC power source (e.g., 120 VAC). The voltage from the input filter and rectifier 110 is stepped down by the AC/DC converter 202 so that low DC voltage (e.g., 12 VDC) is provided to the high voltage power supply 203. The input filter and rectifier 110 also provides DC voltage to the fan speed regulator 205 for the control of the fans 206. The DC voltage (e.g., 160 VDC) supplied to the fan speed regulator 205 is higher than that provided to the high voltage power supply 203. On the other hand, the DC voltage provided by the input filter and rectifier 110 to the voltage control device 131 is stepped down to the same DC voltage (e.g., 12 VDC) being supplied to the high voltage power supply 203.

In FIG. 5, the voltage sensing circuit 212, 213 includes a voltage divider circuit. However, it should be understood that the voltage sensing circuit 221, 213 is not limited to a voltage divider circuit and other voltage measuring circuits or devices for measuring voltage load at the electrode assembly 101 are possible. The voltage divider circuit 212, 213 is used to provide voltage information or data as a voltage signal 215 to the voltage control device 131. This voltage information or data is used by the voltage control device 131 for providing both undervoltage and overvoltage protection of any part of the air treatment apparatus 70. When an undervoltage or an overvoltage condition is detected by the voltage control device 114, 131, the voltage control device 131 is capable of taking corrective actions. By way of example, corrective actions include interrupting power to the electrode assembly 101, and/or energizing an alarming device such as a visible or audible alarm 220. Other corrective actions include performing a conductor drying operation or providing an indication that other actions are required. The voltage control device 131 is also capable of receiving a boost signal 218, which enables the voltage control device to enter a boost mode for a predetermined time period to increase the efficiency of the electrode assembly 101. The boost mode increases efficiency of the electrode assembly by increasing the fan speed as well as increasing the emitter current.

Figure 6:
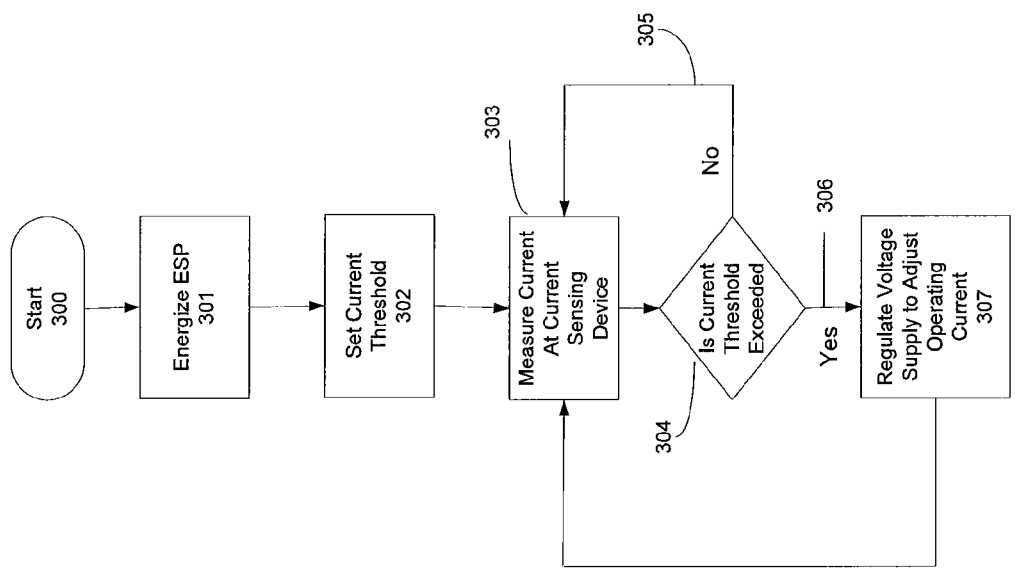
FIG. 6 is a flowchart illustrating one embodiment for using the voltage control circuitry of FIG. 4.

FIG. 6 is a flowchart illustrating an example operation of one embodiment of the voltage control circuitry illustrated in FIG. 4. As illustrated in FIG. 6, the voltage control process is initiated at step 300, which is the result of energizing the electrode assembly at step 301. At step 302, the voltage control device 131 sets a current threshold. The current threshold can relate to designated operating ranges for current flowing in the emitter 103 of the electrode assembly 101, and can vary depending of the control settings set by the voltage control device 131. For example, the voltage control device 131 may set the current threshold based on a LO, MED or HI operating setting of the air treatment apparatus 70. Alternatively, the current threshold can be set at or around virtually any point above the corona threshold, i.e., the voltage level at which ions are generated by the emitter and corona discharge occurs. The current threshold typically represents the current limit or value corresponding to suitable operating efficiency of the air treatment apparatus 70, and designated ozone production ranges.

The high voltage power supply 108, 106 provides increasing AC voltage to the electrode assembly 101 to raise the voltage potential gradient between the emitter 103 and the collector 105. At step 303, the voltage control device 131 measures the current flowing through one or more of the current sensing devices 120, 121, 122, 123, 124, 125. At step 304, the current flowing through the one or more current sensing devices 120, 121, 122, 123, 124, 125 is compared to the current threshold established at step 302. At step 305, if the current is less than the current threshold, the voltage control device 131 continues to measure the current flowing through the one or more current sensing devices 120, 121, 122, 123, 124, 125, as in step 303. However, if at step 306 the current flowing through the one or more current sensing devices 120, 121, 122, 123, 124, 125 exceeds the current threshold, then at a step 307 the voltage control device 131 sends a control signal 117 to the operate the switch 115. Operation of the switch 115 regulates the voltage at the primary winding 109 of the transformer 108, thereby adjusting the operating current in the electrode assembly. Once the initial adjustment of the operating current is complete, the voltage control device 131 continues to measure the current flowing through the one or more current sensing devices 120, 121, 122, 123, 124, 125, as in step 303. In this way, continued adjustments to the current in the electrode assembly can be made.

Figure 7:
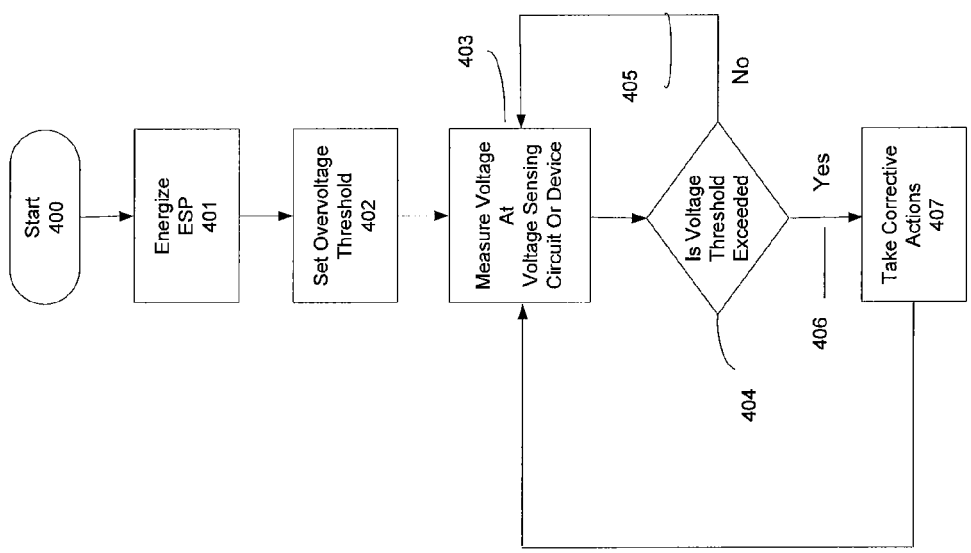
FIG. 7 is a flowchart illustrating one embodiment for using the voltage sensing circuitry of FIG. 5.

FIG. 7 is a flowchart illustrating an example operation of one embodiment of the voltage sensing circuitry illustrated in FIG. 5. As illustrated in FIG. 7, voltage sensing is initiated at step 400, which is the result of energizing the electrode assembly at step 401. At step 402, an overvoltage threshold is set by the voltage control device 131. The overvoltage threshold is related to protecting any portion or part of the air treatment apparatus 70, such as the power supplier 75 or the components in the electrode assembly 101. An over voltage condition may result from, for example, a damaged or missing collector, which could damage to the electrode assembly 101 if operation continues. There can be one or more overvoltage thresholds set by the voltage control device 131 depending on the transient conditions being monitored.

In step 403, the voltage control device 131 measures the voltage at the voltage sensing circuit 212, 213, which is proportional to the voltage at the electrode assembly 101. The voltage sensing circuit 212, 213, in one embodiment, is a voltage divider circuit. The voltage divider circuit 212, 213 provides voltage information or data via as a voltage signal 215 to the voltage control device 131. In step 404, the voltage control device 131 compares the voltage at the voltage sensing circuit 212, 213 with a predetermined voltage threshold.

In step 405, if the measured voltage is less than the voltage threshold, then in step 403 the voltage control device 131 continues to measure the voltage at the sensing circuit 212, 213. However, in step 406, if the voltage measured at the voltage sensing circuit 212, 213 exceeds the threshold, then corrective actions are taken in step 407 to protect one or more parts of the air treatment apparatus 70. In one embodiment, the corrective actions include energizing an alarm, or even shutting down the air treatment apparatus 70. The alarm feature includes an audible or visible alarm 220 as well as other indication that actions are required. An example of required actions can also include servicing or cleaning the air treatment apparatus. Once the corrective actions have been taken, the voltage control device 131 continues to measure the voltage at the voltage sensing circuit 213, 213, as in step 403. Additionally, once the overvoltage condition is corrected, the alarm 220 or indication can be reset. In one embodiment, the voltage control device 131 determines both overvoltage and undervoltage conditions, and takes corrective actions to protect any part or portion of the air treatment apparatus 70.

Figure 8:
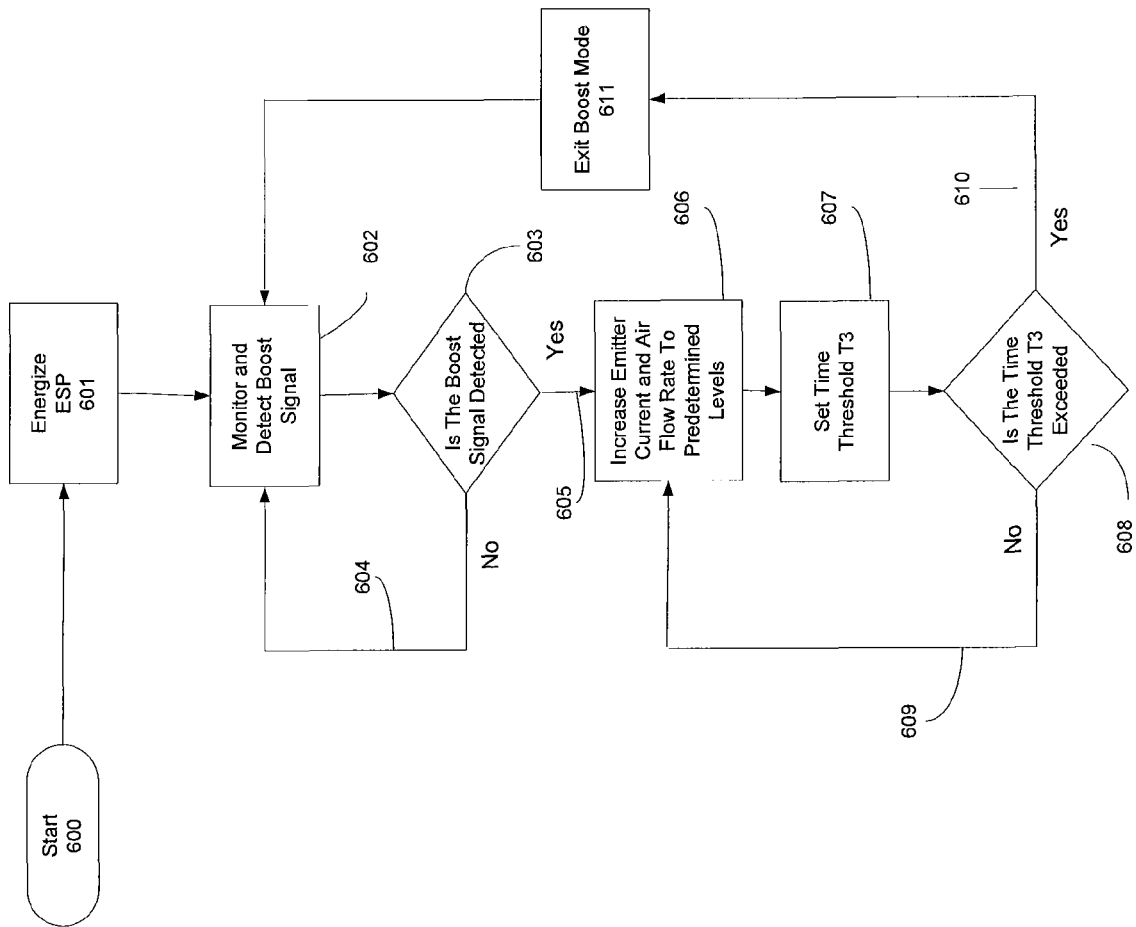
FIG. 8 is a flowchart illustrating one embodiment for boost mode operations for an air treatment apparatus.

FIG. 8 is a flowchart illustrating an example operation of one embodiment of a boost mode of the air treatment apparatus 70. As illustrated in FIG. 6, the boost mode is started at step 600, which can occur when the electrode assembly 101 is energized in step 601 and the voltage control device 131 monitors and detects a boost signal 218 in steps 602. The voltage control device 131 receives a boost signal via the operation of a button or switch on the housing of the air treatment apparatus, or by receiving an automatic signal based on changes in environmental conditions (such as, dust, smoke, odors, fumes, etc.). In step 604, if the voltage control device 131 does not receive a boost signal 218, then the voltage control device 131 continues to monitor for a boost signal, as in step 602. In step 605, if the voltage control device 131 does receive a boost signal 218, then the voltage control device 131, in step 606, will increase the emitter current in the electrode assembly by regulating the high voltage power supply 106, 108, 203. The voltage control device 131 will also increase the fan speed and the air flow rate to the electrode assembly via the fan speed regulator 205.

In step 607, the voltage control device 131 sets a time threshold T3, which relates to the time period for running the air treatment apparatus 70 in the boost mode. By way of example, the boost mode will run for a predetermined time (e.g., 20 minutes). In step 608, the voltage control device 131 will determine if the run time for the boost mode exceeds the threshold T3. In step 609, if the threshold time T3 is not exceeded, then the electrode assembly 101 will continue to run in the boost mode, as in step 606. In step 610, if the current run time for the boost mode exceeds the threshold time T3, then in step 611 the voltage control device 131 exits the boost mode, returns the air treatment apparatus 70 to normal operating mode, and continue to monitor for a boost signal, as in step 602. The normal operating mode can vary depending on the original settings (i.e., Lo, Med. or Hi) of the apparatus.

Controlling voltage in the air treatment apparatus as described in the embodiments above results in improved operating efficiency of the apparatus and ozone production levels within designated ranges. Additionally, negative effects of electrical breakdown or sparking between the emitter and the collector are reduced due to the management of voltage distribution in the electrode assembly based on current sensing. Additionally, such voltage management enables output parameters of the air treatment apparatus to be controlled more accurately and with wider production tolerances.

Mechanical Embodiments

Figure 9:
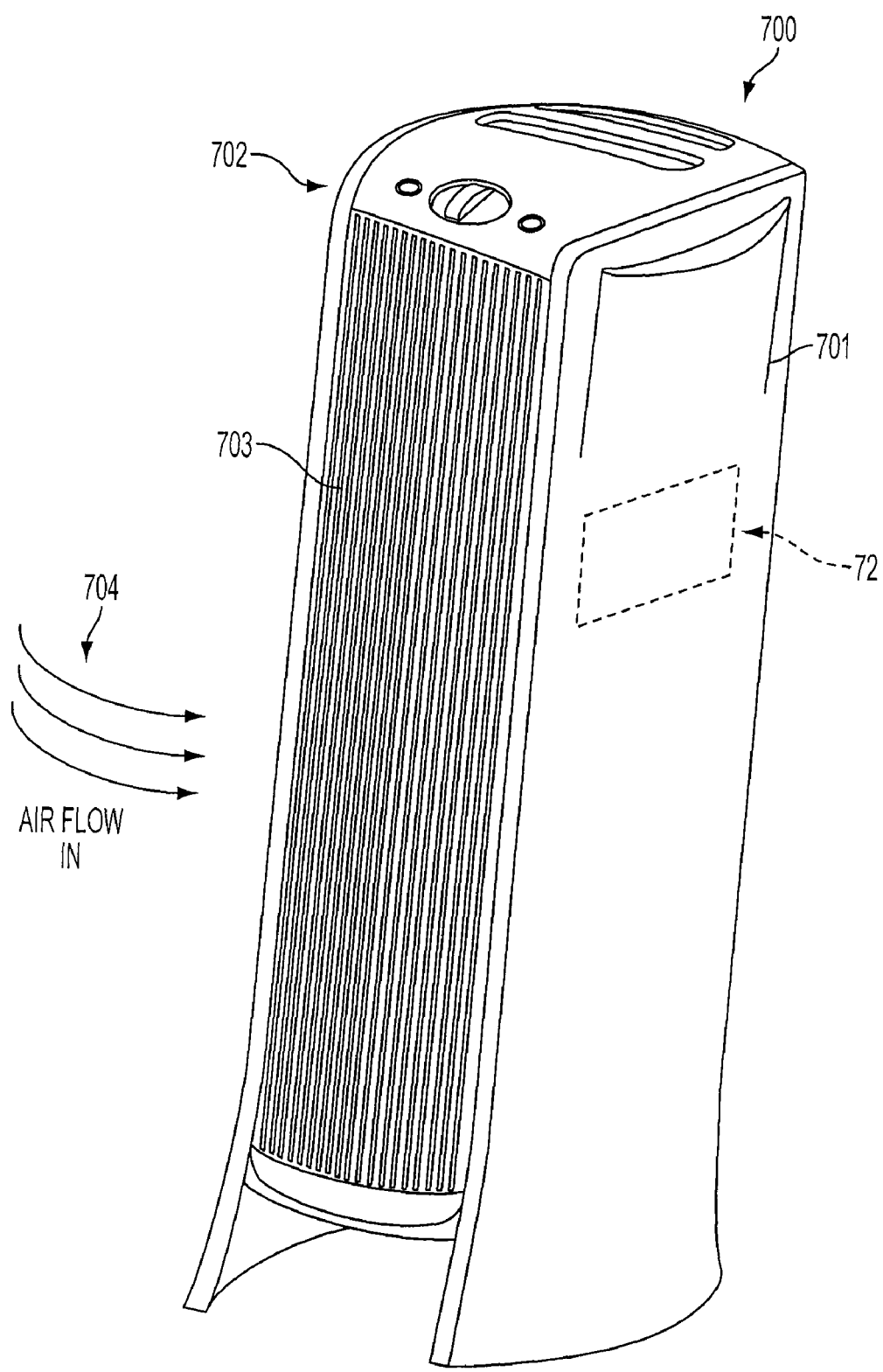
FIG. 9 illustrates a front perspective view of one embodiment of an air treatment apparatus.

In one embodiment illustrated in FIG. 9, the air treatment apparatus 70 is the air treatment apparatus 700. Air treatment apparatus 700 includes an elongated housing 701 which supports the voltage control circuit 72 illustrated in FIG. 1. Though the housing 701 shown has an elongated shape, it should be understood that other shapes for the air treatment apparatus are suitable. The air treatment apparatus 700 includes a control panel 702 for turning on and off the air treatment apparatus 700, or for changing operating settings (e.g., low, medium or high). In operation, the air treatment apparatus 700 draws or forces air in direction 704, and into the apparatus 700 through the front air inlet 703. The font air inlet 703 can include a plurality of fins, slats or louvers that facilitate air flow into the apparatus 700. The electrode assembly 101 in the air treatment apparatus 700 cleans or removes particle from the air as it flows through the apparatus 700. The apparatus 700 can remove dust particles and other airborne particles from the air, including particles which cause odor, as well as particles present in smoke and other gases. Also, the apparatus 700 can condition and treat the air by removing or altering chemicals present in the air. Furthermore, the apparatus can collect or kill airborne pathogens and micro-organisms through the effect of the electric field produced by the electrode assembly 101. Movement of the air through the apparatus and the air cleaning process are similar to that already described with reference to FIG. 4.

Figure 10:
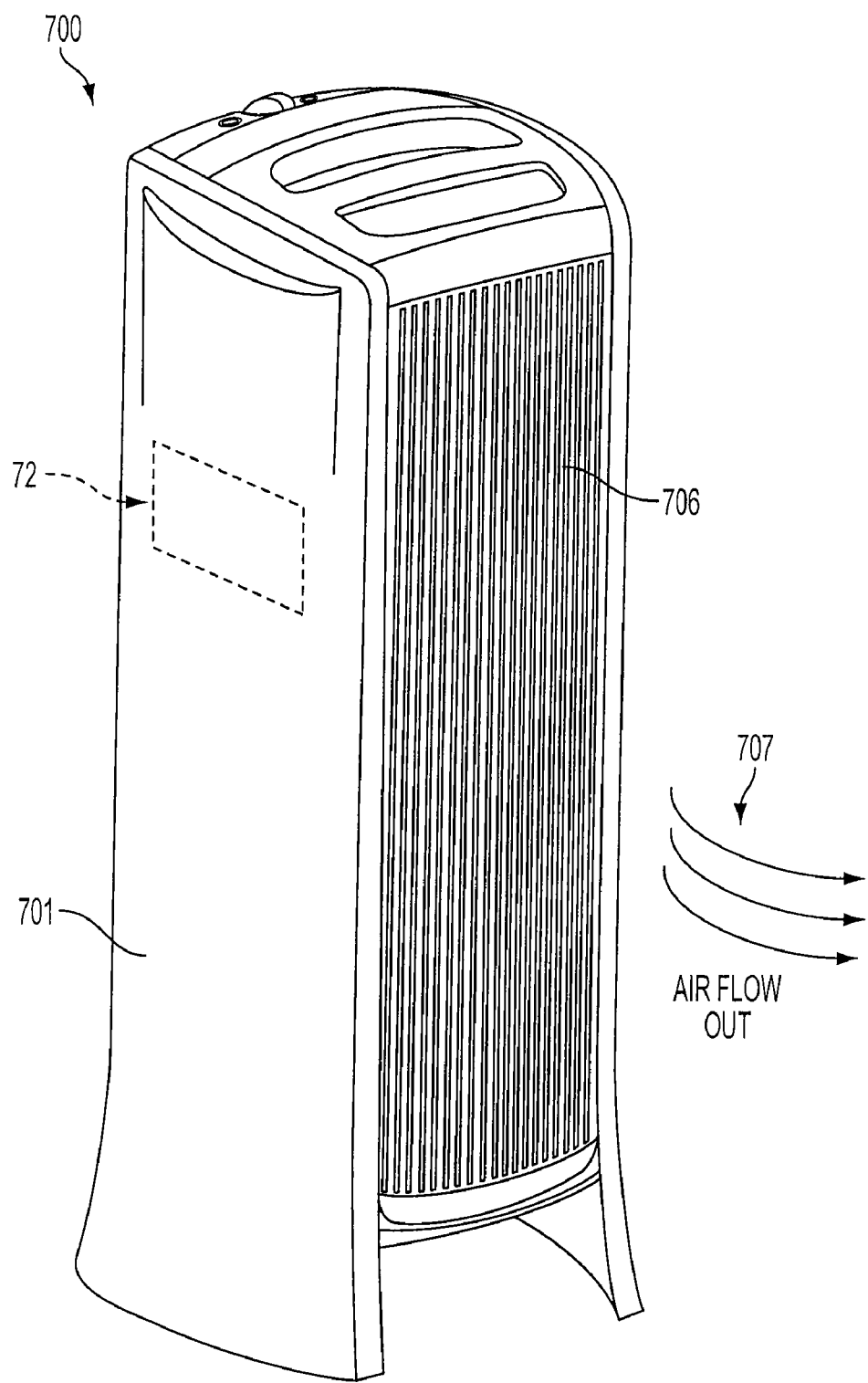
FIG. 10 illustrates a rear perspective view of the air treatment apparatus of FIG. 9.

Once cleaned or otherwise treated, the air exits the apparatus through the rear air outlet 706 illustrated in FIG. 10 in direction 707. Similar to the front air inlet 703, the rear air outlet 706 can include a plurality of fins, slats or louvers that facilitates air flow out of the apparatus 700.

It should be understood that various changes and modifications to the presently preferred embodiments described herein will be apparent to those skilled in the art. Such changes and modifications is made without departing from the spirit and scope of the present invention and without diminishing its intended advantages. It is therefore intended that such changes and modifications be covered by the appended claims.

The invention is claimed as follows:

1. An air treatment apparatus, comprising:
an electrode assembly comprising a plurality of emitter and collector electrodes;
a voltage source coupled to the emitter and collector electrodes for establishing an electric field between the emitter and collector electrodes for producing ozone;
a current sensing device coupled to the electrode assembly for measuring current flowing through the electrode assembly;
a voltage control device coupled to the current sensing device, the voltage control device comprising:
a current input port configured to receive at least one current signal from the current sensing device;
a control output port configured to send at least one voltage control signal to the voltage source in response to the received current signal; and
a control unit operably coupled to the current input port and the control output port, wherein the control unit is configured to:
determine a current value from the received current signal;
determine a designated ozone production range out of a plurality of ozone production ranges of the air treatment apparatus based on the current value; and
provide an appropriate voltage control signal for adjusting the voltage source so as to regulate ozone production by the air treatment apparatus within the designated range.

2. The apparatus of claim 1, wherein the control unit includes at least one of a proportional-integral controller, a proportional-integral-derivative controller, a fuzzy logic controller, a solid state controller, a programmable logic controller, a plurality of discrete electrical components, or analog controller.

3. The apparatus of claim 2, further comprises:
a memory; and
a plurality of instructions stored on the memory, the instructions when executed by at least one controller, causing the control unit to:
(a) measure a current flowing through a current sensing device;
(b) compare the measured current to a current threshold value; and
(c) regulate the voltage source based on the comparison.

4. The apparatus of claim 1, further comprising a voltage sensing circuitry for measuring voltage of the voltage source and providing a voltage input signal to the control unit of the voltage control device.

5. The apparatus of claim 4, further comprising:
a memory; and a plurality of instructions stored on the memory, the instructions when executed by at least one controller, causing the control unit to:
(a) measure the voltage at the voltage source,
(b) compare the measured voltage to a threshold voltage value, and
(c) perform a plurality of corrective actions based on the comparison.

6. The apparatus of claim 5, wherein the control unit is further configured to determining if an undervoltage or overvoltage condition exists at the electrode assembly.

7. The apparatus of claim 5, wherein the corrective actions include increasing the running speed of at least one fan for a predetermined time to produce a higher air flow.

8. The apparatus of claim 5, wherein the corrective actions includes energizing an alarm, providing a visual indication, or interrupting power to the electrode assembly.

9. The apparatus of claim 1, wherein the voltage source includes a transformer having a primary winding and a secondary winding, the primary winding coupled to the control unit and the secondary winding being operably coupled to the electrode assembly.

10. The apparatus of claim 9, wherein the current sensing device is a resistive element configured in a circuit and in series with an emitter electrode of the electrode assembly, a resistive element configured in a circuit and in series with a collector electrode of the electrode assembly, a resistive element configured in a circuit and in series with the primary winding of the transformer, or a resistive element configured in a circuit and in series with the secondary winding of the transformer.

11. The apparatus of claim 9, further comprising a switch connected in series between the control unit and the primary winding of the transformer.

12. The apparatus of claim 1, wherein the current sensing device includes a Hall-effect element, a magnetoresistive sensor, a current transformer, or other electrical device configured to sense current.

13. The apparatus of claim 1, wherein the control unit of the voltage control device is configured to maintain voltage of the voltage source above 4.3 kV.

14. The apparatus of claim 1, wherein the ozone production ranges correspond to current in the electrode assembly within the ranges of 100-600 µA.

* * * * *